United States Patent
Murphy et al.

(10) Patent No.: US 10,967,560 B2
(45) Date of Patent: Apr. 6, 2021

(54) DEVICES, SYSTEMS, AND METHODS FOR THE FABRICATION OF TISSUE

(71) Applicant: Organovo, Inc., San Diego, CA (US)

(72) Inventors: Keith Murphy, Palos Verdes Estates, CA (US); Scott Dorfman, Baltimore, MD (US); Nathan Smith, Ferntree Gully (AU); Larry Bauwens, Lilydale (AU); Ian Sohn, Glen Iris (AU); Tim McDonald, Mount Waverly (AU); Chris Leigh-Lancaster, Murrumbeena (AU); Richard Jin Law, Stamford, CT (US)

(73) Assignee: Organovo, Inc., San Diego, CA (US)

( * ) Notice: Subject to any disclaimer, the term of this patent is extended or adjusted under 35 U.S.C. 154(b) by 88 days.

(21) Appl. No.: 15/816,640

(22) Filed: Nov. 17, 2017

(65) Prior Publication Data
US 2018/0093015 A1 Apr. 5, 2018

Related U.S. Application Data

(63) Continuation of application No. 14/950,567, filed on Nov. 24, 2015, now Pat. No. 9,855,369, which is a (Continued)

(51) Int. Cl.
*B29C 64/106* (2017.01)
*C12M 3/00* (2006.01)
(Continued)

(52) U.S. Cl.
CPC .......... *B29C 64/106* (2017.08); *B01L 3/0268* (2013.01); *B28B 1/001* (2013.01);
(Continued)

(58) Field of Classification Search
CPC ..... B29C 64/106; B29C 64/20; B29C 64/112; B01L 3/0268; B33Y 30/00; B33Y 50/02;
(Continued)

(56) References Cited

U.S. PATENT DOCUMENTS

| | | |
|---|---|---|
| 4,759,764 A | 7/1988 | Fawcett et al. |
| 4,808,435 A | 2/1989 | Cropp et al. |

(Continued)

FOREIGN PATENT DOCUMENTS

| | | |
|---|---|---|
| CA | 2306346 A1 | 1/1999 |
| EP | 2090584 A1 | 8/2009 |

(Continued)

OTHER PUBLICATIONS

ATCC Product Catalog MCF7 (ATCC® HTB-22TM) https://www.atcc.org/products/all/HTB-22.aspx?slp=1#generalinformation, retrieved Sep. 18, 2015.
(Continued)

*Primary Examiner* — Huan H Tran
*Assistant Examiner* — Alexander D Shenderov
(74) *Attorney, Agent, or Firm* — Sterne, Kessler, Goldstein & Fox P.L.L.C.

(57) ABSTRACT

Described herein are bioprinters comprising: one or more printer heads, wherein a printer head comprises a means for receiving and holding at least one cartridge, and wherein said cartridge comprises contents selected from one or more of: bio-ink and support material; a means for calibrating the position of at least one cartridge; and a means for dispensing the contents of at least one cartridge. Further described herein are methods for fabricating a tissue construct, comprising: a computer module receiving input of a visual representation of a desired tissue construct; a computer module generating a series of commands, wherein the commands are based on the visual representation and are read-
(Continued)

able by a bioprinter; a computer module providing the series of commands to a bioprinter; and the bioprinter depositing bio-ink and support material according to the commands to form a construct with a defined geometry.

21 Claims, 5 Drawing Sheets

Related U.S. Application Data continuation of application No. 14/530,499, filed on Oct. 31, 2014, now Pat. No. 9,227,339, which is a continuation of application No. 13/968,313, filed on Aug. 15, 2013, now Pat. No. 8,931,880, which is a continuation of application No. 13/246,428, filed on Sep. 27, 2011, now Pat. No. 9,149,952.

(60) Provisional application No. 61/405,582, filed on Oct. 21, 2010.

(51) Int. Cl.
  *C12M 1/26* (2006.01)
  *B41J 3/407* (2006.01)
  *B29C 64/20* (2017.01)
  *B28B 1/00* (2006.01)
  *B33Y 30/00* (2015.01)
  *B01L 3/02* (2006.01)
  *B33Y 50/02* (2015.01)
  *B33Y 70/00* (2020.01)

(52) U.S. Cl.
  CPC .............. *B29C 64/20* (2017.08); *B33Y 30/00* (2014.12); *B41J 3/407* (2013.01); *C12M 21/08* (2013.01); *C12M 33/00* (2013.01); *B33Y 50/02* (2014.12); *B33Y 70/00* (2014.12)

(58) Field of Classification Search
  CPC ....... B33Y 70/00; C12M 33/00; C12M 21/08; B28B 1/001; B41J 3/407
  USPC .......................................................... 347/20
  See application file for complete search history.

(56) References Cited

U.S. PATENT DOCUMENTS

| | | | |
|---|---|---|---|
| 5,099,090 A | 3/1992 | Allan et al. | |
| 6,315,469 B1 | 11/2001 | Alvarez et al. | |
| 6,401,795 B1 | 6/2002 | Cesarano, III et al. | |
| 6,454,972 B1 | 9/2002 | Morisette et al. | |
| 6,520,997 B1 | 2/2003 | Pekkarinen et al. | |
| 6,537,567 B1 | 3/2003 | Niklason et al. | |
| 6,561,607 B1 | 5/2003 | Lubinsky et al. | |
| 6,568,787 B1 | 5/2003 | Girones et al. | |
| 6,642,243 B1 | 11/2003 | Imanzahrai | |
| 6,713,772 B2 | 3/2004 | Goodman et al. | |
| 6,939,489 B2 | 9/2005 | Moszner et al. | |
| 6,942,830 B2 | 9/2005 | Muelhaupt et al. | |
| 6,979,670 B1 | 12/2005 | Lyngstadaas et al. | |
| 6,986,739 B2 | 1/2006 | Warren et al. | |
| 7,051,654 B2 | 5/2006 | Boland et al. | |
| 7,196,842 B2 | 3/2007 | Weigl et al. | |
| 7,484,837 B2 | 2/2009 | Koga et al. | |
| 7,625,198 B2 | 12/2009 | Lipson et al. | |
| 7,651,665 B2 | 1/2010 | Gonzalez et al. | |
| 7,680,555 B2 | 3/2010 | Dunn et al. | |
| 7,767,446 B2 | 8/2010 | Robbins et al. | |
| 7,887,843 B2 | 2/2011 | Libera et al. | |
| 7,980,645 B2 | 7/2011 | Ohtsuka et al. | |
| 8,143,055 B2 | 3/2012 | Forgacs et al. | |
| 8,241,905 B2 | 8/2012 | Forgacs et al. | |
| 8,343,740 B2 | 1/2013 | Gonda et al. | |
| 8,580,546 B2 | 11/2013 | Gonda et al. | |
| 8,728,807 B2 | 5/2014 | Forgacs et al. | |
| 8,747,880 B2 | 6/2014 | Forgacs et al. | |
| 8,852,932 B2 | 10/2014 | Forgacs et al. | |
| 8,931,880 B2 | 1/2015 | Murphy et al. | |
| 9,149,952 B2 | 10/2015 | Murphy et al. | |
| 2001/0042942 A1 | 11/2001 | Hizumi et al. | |
| 2002/0171178 A1 | 11/2002 | Dean et al. | |
| 2002/0182633 A1 | 12/2002 | Chen et al. | |
| 2002/0188349 A1 | 12/2002 | McAllister et al. | |
| 2003/0049839 A1 | 3/2003 | Romero-Ortega et al. | |
| 2003/0149505 A1 | 8/2003 | Mogensen | |
| 2003/0153078 A1 | 8/2003 | Libera et al. | |
| 2003/0175410 A1 | 9/2003 | Campbell et al. | |
| 2003/0236588 A1 | 12/2003 | Jang et al. | |
| 2004/0006405 A1 | 1/2004 | Chen et al. | |
| 2004/0132184 A1 | 7/2004 | Dennis et al. | |
| 2004/0197367 A1 | 10/2004 | Rezania et al. | |
| 2004/0219133 A1 | 11/2004 | Lyles | |
| 2004/0237822 A1 | 12/2004 | Boland et al. | |
| 2004/0253365 A1 | 12/2004 | Warren et al. | |
| 2005/0009178 A1 | 1/2005 | Yost et al. | |
| 2005/0091576 A1 | 4/2005 | Relyea et al. | |
| 2005/0169962 A1 | 8/2005 | Bhatia et al. | |
| 2005/0226856 A1 | 10/2005 | Ahlfors | |
| 2005/0276791 A1 | 12/2005 | Hansford et al. | |
| 2006/0099287 A1 | 5/2006 | Kim et al. | |
| 2006/0198918 A1 | 9/2006 | Koyagi et al. | |
| 2006/0237880 A1 | 10/2006 | Wicker et al. | |
| 2006/0270032 A1 | 11/2006 | Bhatia et al. | |
| 2007/0086986 A1 | 4/2007 | Vigo et al. | |
| 2007/0108229 A1* | 5/2007 | Fork | B05B 9/06 222/129 |
| 2007/0142916 A1 | 6/2007 | Olson, Jr. et al. | |
| 2007/0200276 A1 | 8/2007 | Mackey et al. | |
| 2007/0231787 A1 | 10/2007 | Voelker | |
| 2007/0299508 A1 | 12/2007 | Morrison et al. | |
| 2008/0027114 A1 | 1/2008 | Funke et al. | |
| 2008/0070304 A1* | 3/2008 | Forgacs | C12N 5/0062 435/397 |
| 2008/0097575 A1 | 4/2008 | Cottone | |
| 2008/0192074 A1 | 8/2008 | Dubois et al. | |
| 2008/0193910 A1 | 8/2008 | Larkin et al. | |
| 2009/0076531 A1 | 3/2009 | Richardson et al. | |
| 2009/0117087 A1 | 5/2009 | Carroll et al. | |
| 2009/0142307 A1 | 6/2009 | Athanasiou et al. | |
| 2009/0206522 A1 | 8/2009 | Hein et al. | |
| 2009/0208466 A1 | 8/2009 | Yoo et al. | |
| 2009/0208577 A1 | 8/2009 | Xu et al. | |
| 2009/0239302 A1 | 9/2009 | Decher et al. | |
| 2009/0248145 A1 | 10/2009 | Chan et al. | |
| 2009/0263849 A1 | 10/2009 | Sun et al. | |
| 2009/0267269 A1 | 10/2009 | Lim et al. | |
| 2010/0056390 A1 | 3/2010 | Fischbach | |
| 2010/0160183 A1 | 6/2010 | Xu et al. | |
| 2010/0191360 A1 | 7/2010 | Napadensky et al. | |
| 2010/0254900 A1 | 10/2010 | Campbell et al. | |
| 2011/0064784 A1 | 3/2011 | Mullens et al. | |
| 2011/0172611 A1 | 7/2011 | Yoo et al. | |
| 2011/0180914 A1 | 7/2011 | Do et al. | |
| 2011/0212501 A1 | 9/2011 | Yoo | |
| 2011/0250688 A1 | 10/2011 | Hasan | |
| 2012/0045770 A1 | 2/2012 | Pongracz et al. | |
| 2012/0089238 A1 | 4/2012 | Kang et al. | |
| 2013/0084449 A1 | 4/2013 | Lewis et al. | |
| 2013/0108726 A1 | 5/2013 | Uckelmann et al. | |
| 2013/0164339 A1 | 6/2013 | Murphy et al. | |
| 2013/0190210 A1 | 7/2013 | Murphy et al. | |
| 2013/0193619 A1 | 8/2013 | Church et al. | |
| 2013/0236431 A1 | 9/2013 | Gourdie et al. | |
| 2013/0236879 A1 | 9/2013 | Berry et al. | |
| 2013/0345794 A1 | 12/2013 | Khatiwala et al. | |
| 2014/0012225 A1 | 1/2014 | Yoo et al. | |
| 2014/0044822 A1 | 2/2014 | Mulliken | |
| 2014/0093932 A1 | 4/2014 | Murphy et al. | |
| 2014/0099709 A1 | 4/2014 | Presnell et al. | |
| 2014/0131313 A1 | 5/2014 | Wakamatsu et al. | |
| 2014/0220685 A1 | 8/2014 | Forgacs et al. | |
| 2014/0265049 A1 | 9/2014 | Burris et al. | |

(56) References Cited

U.S. PATENT DOCUMENTS

| | | |
|---|---|---|
| 2014/0274802 A1 | 9/2014 | Shepherd et al. |
| 2014/0287960 A1 | 9/2014 | Shepherd et al. |
| 2014/0358273 A1 | 12/2014 | Labossiere et al. |
| 2015/0004273 A1 | 1/2015 | Forgacs et al. |
| 2015/0037445 A1 | 2/2015 | Murphy et al. |
| 2015/0057786 A1 | 2/2015 | Murphy et al. |
| 2015/0282885 A1 | 10/2015 | King et al. |
| 2015/0314613 A1 | 11/2015 | Murphy et al. |
| 2015/0344828 A1 | 12/2015 | Forgacs et al. |

FOREIGN PATENT DOCUMENTS

| | | |
|---|---|---|
| JP | 2001038981 A | 2/2001 |
| JP | 2005031144 A | 2/2005 |
| JP | 2006159117 A | 6/2006 |
| KR | 20090087748 A | 8/2009 |
| RU | 2371758 C2 | 10/2009 |
| WO | WO-9901538 A1 | 1/1999 |
| WO | WO-0168811 A2 | 9/2001 |
| WO | WO-2004108418 A1 | 12/2004 |
| WO | WO-2005025493 A2 | 3/2005 |
| WO | WO-2005081970 A2 | 9/2005 |
| WO | WO-2007076272 A2 | 7/2007 |
| WO | WO-2007115336 A2 | 10/2007 |
| WO | WO-2007115337 A2 | 10/2007 |
| WO | WO-2007124023 A2 | 11/2007 |
| WO | WO-2007125893 A1 | 11/2007 |
| WO | WO-2007126411 A2 | 11/2007 |
| WO | WO-2007136936 A2 | 11/2007 |
| WO | WO-2009102484 A2 | 8/2009 |
| WO | WO-2009154466 A1 | 12/2009 |
| WO | WO-2010008905 A2 | 1/2010 |
| WO | WO-2011038373 A2 | 3/2011 |
| WO | WO-2011088213 | 7/2011 |
| WO | WO-2011097330 A2 | 8/2011 |
| WO | WO-2011107599 A1 | 9/2011 |
| WO | WO-2011119059 A1 | 9/2011 |
| WO | WO-2012003465 A2 | 1/2012 |
| WO | WO-2012054195 A2 | 4/2012 |
| WO | WO-2012131000 A1 | 10/2012 |
| WO | WO-2013130823 A1 | 9/2013 |
| WO | WO-2013192290 A1 | 12/2013 |

OTHER PUBLICATIONS

ATCC Product catalog Primary Subcutaneous Pre-adipocytes; Normal, Human (ATCC® PCS-210-01OTM) https://www.atcc.org/Products/All/PCS-210-010.aspx?slp=1, retrieved Sep. 18, 2015.
Baltich et al. Development of a Scaffoldless Three-Dimensional Engineered Nerve Using a Nerve-Fibroblast Co-Culture. In Vitro Cell. Dev. Biol.—Animal 46:438-444 (2010).
Bioscaffolder 2008, www.syseng.de, SYSENG Dipl.-ing. Hendrik John.
Boland et al. Application of inkjet printing to tissue engineering. Biotech J. 1:910-917 (2006).
Boland et al. Cell and Organ Printing 2: Fusion of Cell Aggregates in Three-Dimensional Gels. The Anatomical Record, Part A. 272A:497-502 (2003).
Bunnell et at. Adipose-derived Stem Cells: Isolation, Expansion and Differentiation. Methods 45(2):115-120 (2008).
Chaterji et al. Scaffold-Free In Vitro Arterial Mimetics: The Importance of Smooth Muscle-Endothelium Contact. Tissue Engineering Part A 16(8):1901-1912 (2010).
Sciperio, Inc. 2003 R&D 100 Award Winner. Sciperio, http://www.sciperio.com/news/20031016.asp, accessed on Feb. 1, 2005, 2 pages.
Constans. Body by Science. The Scientist 17(19):34-37 http://www.the-scientist.com/article/display/141541 (2003).
Co-pending U.S. Appl. No. 14/876,659, filed Oct. 6, 2015.
Co-pending U.S. Appl. No. 14/933,822, filed Nov. 5, 2015.
Co-pending U.S. Appl. No. 14/936,580, filed Nov. 9, 2015.
Cui et al. Direct Human Cartilage Repair Using Three-Dimensional Bioprinting Technology. Tissue Engineering Part A 18(11-12):1304-1312 (2012).
Dai et al. Fibroblast Aggregation by Suspension with Conjugates of Poly(ethylene glycol) and RGD. Biotechnology and Bioengineering 50(4):349-356 (May 20, 1996).
Dirat et al. Cancer-associated adipocytes exhibit an activated phenotype and contribute to breast cancer invasion. Cancer Res. 71(7):2455-2465 (2011).
Dominici et al. Minimal criteria for defining multipotent mesenchymal stromal cells, International Society for Cellular Therapy position statement. Cytotherapy 8(4):315-317 (2006).
Edelman. Vascular Tissue Engineering: Designer Arteries. Circ Res 85(12):1115-1117 (1999).
Egebald et al. Tumors as organs: complex tissues that interface with the entire organism. Dev Cell. 18(6):884-901 (2010).
Eisenberg et al. Bone Marrow Cells Transdifferentiate to Cardiomyocytes When Introduced into the Embryonic Heart. Stem Cells 24:1236-1245 (2006).
Fedorovich et al. Distinct Tissue Formation by Heterogeneous Printing of Osteo- and Endothelial Progenitor Cells. Tissue Engineering: Part A 17(15-16):2113-2123 (2011).
Fedorovich et al. Three-Dimensional Fiber Deposition of Cell-Laden, Viable Patterned Constructs for Bone Tissue Printing, Tissue Engineering: Part A 14(1):127-135 (2008).
Forgacs et al. Biological Relevance of Tissue Liquidity and Viscoelasticity Eds. A. Deutsch, M. Falcke, J. Howard and W. Zimmermann. Birkhauser. pp. 269-277 (2004).
Forgacs et al. Viscoelastic Properties of Living Embryonic Tissues: A Quantitative Study, Biophysical Journal 74(5):2227-2234 (May 1998).
Foty et al. Surface Tensions of Embryonic Tissues Predict Their Mutual Envelopment Behavior. Development 122(5):1611-1620 (1996).
Foty et al. The Differential Adhesion Hypothesis: A Direct Evaluation, Developmental Biology 278(1):255-263 (2005).
Frisman et al. Nanostructuring of PEG-fibrinogen polymeric scaffolds. Acta Biomaterialia 6(7):2518-2524 (2009).
Fuellhase et al. 264 Generation of Organized Bladder Tissue Constructs Using a Novel Hybrid Printing System. European Urology Supplements 8(4):186 (2009).
Fujita et al. Fabrication of scaffold-free contractile skeletal muscle tissue using magnetite-incorporated myogenic C2C12 cells. J Tissue Eng Regen Med. 4(6):437-443 (2010).
Furukawa et al. Formation of Human Fibroblast Aggregates (Spheroids) by Rotational Culture. Cell Transplantation 10(4-5):441-445 (2001).
Furukawa et al. Scaffold-free cartilage tissue by mechanical stress loading for tissue engineering. In Tissue Engineering, ed by Daniel Eberli. InTech p. 409-428 (2010).
Furukawa et al. Tissue-engineered Skin Using Aggregates of Normal Human Skin Fibroblasts and Biodegradable Material. J. MK Organs 4:353-356 (2001).
Ghorbanian et al. Microfluidic direct writer with integrated declogging mechanism for fabricating cell-laden hydrogel constructs. Biomed Microdevices (doi: 10.1007/s10544-014-9842-8), Springer Science+Business Media New York 2014 (Mar. 4, 2014).
Glazier et al. Simulation of the Differential Adhesion Driven Rearrangement of Biological Cells. Physical Review E 47(3):2128-2154 (Mar. 1993).
Glicklis et al. Modeling Mass Transfer in Hepatocyte Spheroids Via Cell Viability, Spheroid Size, and Hepatocellular Functions. Biotechnology and Bioengineering 86(6):672-680 (Jun. 20, 2004).
Graner et al. Simulation of Biological Cell Sorting Using a Two-Dimensional Extended Potts Model, Physical Review Letters 69(13):2013-2016 (Sep. 28, 1992).
Grange et al. Isolation and characterization of human breast tumor-derived endothelial cells. Oncol Rep. 15(2):381-386 (2006).
Gruene et al. Laser Printing of Stem Cells for Biofabrication of Scaffold-Free Autologous Grafts. Tissue Engineering: Part C 17(1):79-89 (2011).
Gruene et al. Laser printing of three-dimensional multicellular arrays for studies of cell-cell and cell-environment interactions. Tissue Eng Part C Methods 17(10):973-82 (Oct. 2011).

(56) References Cited

OTHER PUBLICATIONS

Guenard et al. Syngeneic Schwann Cells Derived from Adult Nerves Seeded in Semipermeable Guidance Channels Enhance Peripheral Nerve Regeneration. The Journal of Neuroscience 12(9):3310-3320 (Sep. 1992).
Guillemot et al. High-throughput laser printing of cells and biomaterials for tissue engineering. Acta biomaterialia 6:2494-2500 (2010).
Hadlock et al. A Polymer Foam Conduit Seeded with Schwann Cells Promotes Guided Peripheral Nerve Regeneration, Tissue Engineering 6(2):119-127 (2000).
Halley et al. Growing Organs in the Lab. Longevity. 1-7 (Jun. 2009).
Harvey et al. Schwann cells and fetal tectal tissue cografted to the midbrain of newborn rats: fate of Schwann cells and their influence on host retinal innervation of grafts. Exp Neurol. 134(2):179-91 (1995).
Hierlihy et al. The post-natal heart contains a myocardial stem cell population. FEBS Letters 530:239-243 (2002).
Hockaday et al. Rapid 3D printing of anatomically accurate and mechanically heterogeneous aortic valve hydrogel scaffolds. Biofabrication 4(3):1-12 (2012).
Hubbard et al. Bioengineered, Autologous, Scaffold-free Nerve Conduit for Peripheral Nerve Repair. Abstract. AAHS/ASPN/ASRM 2011, Annual Scientific Meetings Program Book. pp. 140 and 159 (Jan. 12-18, 2011).
Ito et al. Novel Methodology for Fabrication of Tissue-Engineered Tubular Constructs Using Magnetite Nanoparticles and Magnetic Force, Tissue Engineering, Larchmont, NY, US, 11(9-10):1553-1561 (2005).
Iwasaki et al. Bioengineered Three-Layered Robust and Elastic Artery Using Hemodynamically-Equivalent Pulsatile Bioreactor. Circulation 18(14 Suppl):S53-S57 (2008).
Izaguirre et al. CompuCell, a multi-model framework for simulation of morphogenesis. Bioinformatics 20(7):1129-1137 (2004).
Jakab et al. Engineering Biological Structures of Prescribed Shape Using Self-assembling Multicellular Systems. PNAS USA 101:2864-2869 (2004).
Jakab et al. Organ printing: fiction or science. Biorheology 43(3-4):371-375 (2004).
Jakab et al. Relating Cell and Tissue Mechanics: Implications and Applications. Developmental Dynamics 237:2438-2449 (2008).
Jakab et al. Three-dimensional tissue constructs built by bioprinting. Biorheology 43(3-4):509-513 (2006).
Jakab et al. Tissue Engineering by Self-Assembly and Bio-printing of living cells. Biofabrication 2(2):022001 (14 pp) (Jun. 2, 2010).
Jakab et al. Tissue Engineering by Self-Assembly of Cells Printed into Topologically Defined Structures. Tissue Engineering: Part A. 14:413-421 (Nov. 3, 2008).
Kasko. Degradable Poly(ethylene glycol) Hydrogels for 2D and 3D Cell Culture. Aldrich Materials Science, pp. 67-75 (no date available).
Kelm et al. Design of Custom-Shaped Vascularized Tissues Using Microtissue Spheroids as Minimal Building Units. Tissue Engineering 12(8):2151-2160 (2006).
Kelm et al. Microscale Tissue Engineering Using Gravity-Enforced Cell Assembly. TRENDS in Biotechnology 22(4):195-202 (Apr. 2004).
Khatiwala et al. 3D Cell Bioprinting for Regenerative Medicine Research and Therapies. Gene Therapy and Regulation 7(1):1-19 (2012).
King et al. Development of 3D bioprinted human breast cancer for in vitro screening of therapeutics targeted against cancer progression. IEEE The American Society for Cell biology. 2013 ascb annual meeting. New Orleans: IEEE Dec. 14-18, 2013.
Koibuchi et al. Behavior of Cells in Artificially Made Cell Aggregates and Tissue Fragments after Grafting to Developing Hind Limb Buds in Xenopus laevis. The International Journal of Developmental Biology 43(2):141-148 (1999).
Korff et al. Blood Vessel Maturation in a 3-Dimensional Spheroidal Coculture Model: Direct Contact with Smooth Muscle Cells Regulates Endothelial Cell Quiescence and Abrogates VEGF Responsiveness. The FASEB Journal 15:447-457 (Feb. 2001).
Landers et al. Fabrication of soft tissue engineering scaffolds by means of rapid prototyping techniques. Journal of Materials Science 37:3107-3116 (2002).
Larkin et al. Structure and Functional Evaluation of Tendon-Skeletal Muscle Constructs Engineered in Vitro. Tissue Eng. 12(11):3149-3158 (Nov. 2006).
Lee et al. Multi-layered Culture of Human Skin Fibroblasts and Keratinocytes Through Three-dimensional Freeform Fabrication. Biomaterials 30:1587-1595 (2009).
L'Heureux et al. A completely biological tissue-engineered human blood vessel. The FASEB Journal 12 (1):47-56 (1998).
L'Heureux et al. Human tissue-engineered blood vessels for adult arterial revascularization. Nature Medicine 12 (3):361-365 (2006).
L'Heureux et al. Sheet-Based Tissue Engineering From Bench Top to the First Clinical Use of a Completely Biological Tissue Engineered Vessel. The FASEB Journal 12(1):47-56 (Abstract) (2006).
Liu et al. Design and Development of Three-Dimensional Scaffolds for Tissue Engineering. Chemical Engineering Research and Design 85(7):1051-1064 (2007).
Luo et al. Three-dimensional microtissue assay for high-throughput cytotoxicity of nanoparticles. Anal Chem. 84(15):6731-6738 (Aug. 7, 2012).
Marga et al. Bioprint Engineered Fully Biological Nerve Graft. Poster Presentation TERMIS Dec. 5-8, 2010, Orlando, Florida, 1 page.
Marga et al. Construction of a Bioprinted Fully Biological Nerve Graft. Biophysical Journal 96(3 supp 1):643a Abstract (Feb. 2009).
Marga et al. Developmental Biology and Tissue Engineering, Birth Defects Research (Part C) 81:320-328 (2007).
Marga et al. Engineered Fully Biological Nerve Graft. Poster Presentation Biophysical Society Meeting, Mar. 4, 2009, 1 page.
Marga et al. Toward Engineering Functional Organ Modules by Additive Manufacturing. Biafabrication 4:022001 (12 pp) (2012).
Martin et al. Computer-Based Technique for Cell Aggregation Analysis and Cell Aggregation in In Vitro Chondrogenesis. Cytometry 28(2):141-146 (1997).
McGuigan et al. Vascularized organoid engineered by modular assembly enables blood perfusion. PNAS, 103(31):11461-11466 (2006).
Mehesz et al. Scalable robotic biofabrication of tissue spheroids. Biofabrication 3:1-8 (2011).
Mironov et al. Bioprinting Living Structures. J. Mat. Chem. 17:2054-2060 (2007).
Mironov et al. Organ Printing: Computer-Aided Jet-Based 3D Tissue Engineering. TRENDS in Biotechnology 21(4):157-161 (Apr. 2003).
Mironov et al. Organ Printing: Self-Assembling Cell Aggregates as 'Bioink'. Science & Medicine 9(2):69-71 (Apr. 2003).
Mironov et al. Organ Printing: Tissue Spheroids as Building Blocks. Biomaterials 30:2164-2174 (2009).
Mizumoto et al. Formation of Cylindrical Multicellular Aggregate (Cylindroid) and Express of Liver Specific Functions of Primary Rat Hepatocytes. Cytotechnology 31:69-75 (1999).
Mombach et al. Quantitative Comparison Between Differential Adhesion Models and Cell Sorting in the Presence and Absence of Fluctuations. Physical Review Letters 75(11):2244-2247 (Sep. 11, 1995).
Moon et al. Layer by Layer Three-dimensional Tissue Epitaxy by Cell-Laden Hydrogel Droplets. Tissue Engineering Part C: Methods 16(1):157-166 (2010).
Mroue et al. Three-dimensional cultures of mouse mammary epithelial cells. Methods Mol Biol. 945:221-250 (2013).
Neagu et al. Role of physical mechanisms in biological self-organization. Phys RevLett 95(17):178104 (2005).
Newman et al. Before programs: the physical origination of multicellular forms, Int J Dev Biol. 50(2-3):289-299 (2006).
Nickerson et al. Three-Dimensional Tissue Assemblies: Novel Models for the Study of *Salmonella enterica* Serovar Typhimurium Pathogenesis. Infection and Immunity 69(11):7106-7120 (Nov. 2001).
Niklason et al. Advances in Tissue Engineering of Blood Vessels and Other Tissues. Transpl. Immunol. 5(4):303-306 (1997).

(56) References Cited

OTHER PUBLICATIONS

Norotte et al. Scaffold-free vascular tissue engineering using bioprinting. Biomaterials 30:5910-5917 (2009).
Panagiotis et al. A unique aged human retinal pigmental epithelial cell line useful for studying lens differentiation in vitro. International Journal of Developmental Biology 45:753-758 (2001).
Pathology Outlines: Bladder. Normal Histology. pp. 1-4 (2011).
Paul et al. How to improe R&D productivity: the pharmaceutical industry's grand challenge. Nature Reviews Drug Discovery 9(3):203-214 (2010).
PCT/US2005/05735 International Search Report dated Dec. 7, 2007.
PCT/US2005/05735 International Preliminary Report on Patentability dated Mar. 3, 2009.
PCT/US2009/48530 International Preliminary Report on Patentability dated Jan. 13, 2011.
PCT/US2009/48530 International Search Report dated Mar. 15, 2010.
PCT/US2011/023520 International Preliminary Report on Patentability dated Aug. 16, 2012.
PCT/US2011/023520 International Search Report dated Oct. 31, 2011.
PCT/US2011/028713 International Preliminary Report on Patentability dated Sep. 18, 2012.
PCT/US2011/028713 International Search Report dated Nov. 30, 2011.
PCT/US2011/053515 International Preliminary Report on Patentability dated May 3, 2013.
PCT/US2011/053515 International Search Report and Written Opinion dated May 1, 2012.
PCT/US2012/054923 International Preliminary Report on Patentability dated Mar. 20, 2014.
PCT/US2012/054923 International Search Report dated Feb. 26, 2013.
PCT/US2012/054935 International Preliminary Report on Patentability dated Mar. 20, 2014.
PCT/US2012/054935 International Search Report dated Feb. 28, 2013.
PCT/US2013/036479 International Preliminary Report on Patentability dated Oct. 21, 2014.
PCT/US2013/036479 International search report dated Jul. 25, 2013.
PCT/US2013/046519 International Preliminary Report on Patentability dated Dec. 23, 2014.
PCT/US2013/046519 International Search Report dated Sep. 5, 2013.
PCT/US2014/026679 International Preliminary Report on Patentability dated Sep. 24, 2015.
PCT/US2014/026679 International Search Report and Written Opinion dated Jul. 22, 2014.
PCT/US2014/041419 International Search Report and Written Opinion dated Jan. 2, 2015.
PCT/US2014/048962 International Search Report and Written Opinion dated Nov. 10, 2014.
Pearson Education. Human Heart Illustration (2004).
Perez-Pomares et al. Tissue Fusion and Cell Sorting in Embryonic Development and Disease: Biomedical Implications. Bioessays 28:809-821 (2006).
Remuzzi et al. Vascular Smooth Muscle Cells on Hyaluronic Acid: Culture and Mechanical Characterization of an Engineered Vascular Construct. Tissue Engineering 10(516):699-710 (2004).
Riken. Self-healing hydrogels ease into production. Research Highlights: Materials. Downloaded from the Riken website: <http://www.riken.jp/en/research/rikenresearch/highlights/7543/> (Nov. 1, 2013) [accessed Apr. 27, 2015].
Ryan et al. Tissue Spreading on Implantable Substrates is a Competitive Outcome of Cell-Cell vs. Cell-Substratum Adhesivity. PNAS 98(8):4323-4327 (Apr. 10, 2001).
Schuster et al. Why Drugs Fail—A Study on Side Effects in New Chemical Entities. Curr. Pharm. Des. 11:3545 (2005).
Shafrir et al. Mechanotransduction through the cytoskeleton. American Journal of Physiology 282:479-486 (2002).
Sheehan et al. Recent Patents and Trends in Bioprinting. Recent Patents on Biomedical Engineering 4:26-32 (2011).
Shim et al. Bioprinting of a mechanically enhanced three-dimensional dual cell-laden construct for osteochondral tissue engineering using a multi-head tissue/organ building system. J of Micromechanics and Microengineering. 22(Article No. 085014):1-11 (2012).
Siemionow et al. Current Techniques and Concepts in Peripheral Nerve Repair. Chapter 8, International Review of Neurobiology, 87:141-172 (2009).
Skardal et al. Bioprinting vessel-like constructs using hyaluronan hydrogels crosslinked with tetrahedral polyethylene glycol tetracrylates. Biomaterials 31:6173-6181 (2010).
Smith. A direct-write three-dimensional Bioassernbly tool for regenerative medicine. The University of Arizona pp. 1-291 (Nov. 1, 2005).
Smith et al. Characterizing Environment Factors that Impact the Viability of Tissue-Engineered Constructs Fabricated by a Direct-Write Bioassembly Tool. Tissue Engineering, 13(2):373-385 (2007).
Smith et al. Three-Dimensional BioAssernbly Tool for Generating Viable Tissue-Engineered Constructs. Tissue Engineering 10(9/10):1566-1576 (2004).
Steinberg. Does Differential Adhesion Govern Self-Assembly Processes in Histogenesis? Equilibrium Configurations and the Emergence of a Hierarchy Among Populations of Embryonic Cells. The Journal of Experimental Zoology 173(4):395-433 (Apr. 1970).
Steinberg et al. Liquid Behavior of Embryonic Tissues. Cell Behaviour pp. 583-697 (1982).
Stiles. UA Wins R & D 100 Award for Machine that Prints Tissue Cell-by-Cell. UANews Dec. 2, 2003, http://uanews.org/cgi-binfflebObjects/UANews.woa/wa/goPrint?ArticleID=8305, accessed on Feb. 1, 2005, 2 pages.
Tanaka et al. A Valved Hepatic Portoduodenal Instestinal Conduit for Biliary Atresia. Ann. Surg. 213(3):230-235 (1991).
Tang et al. Molding of Three-Dimensional Microstructures of Gels. Journal of the American Chemical Society 125(43):12988-12989 (Oct. 29, 2003).
Tao et al. Bio-printing of living organized tissues using an inkjet technology. Database Accession No. PREV200700335042. FASEB Journal 23(5):A636 (2007).
Timmins et al. Hanging-Drop Multicellular Spheroids as a Model of Tumour Angiogenesis. Angiogenesis 7(2):97-103 (2004).
Tsang et al. Fabrication of 3D hepatic tissues by additive photopatterning of cellular hydrogels. The FASEB Journal 21(3):790-801 (2007).
Tsang. Three-Dimensional Tissue Fabrication, Advanced drug delivery reviews 56(11):1635-1647 (2004).
U.S. Appl. No. 10/590,446 Office action dated Jan. 6, 2011.
U.S. Appl. No. 10/590,446 Office action dated Sep. 1, 2011.
U.S. Appl. No. 10/666,836 Office action dated Oct. 28, 2004.
U.S. Appl. No. 11/227,489 Office action dated Dec. 10, 2008.
U.S. Appl. No. 11/227,489 Office action dated Jul. 8, 2009.
U.S. Appl. No. 13/020,000 Office action dated Dec. 31, 2012.
U.S. Appl. No. 13/020,000 Office action dated Jul. 3, 2013.
U.S. Appl. No. 13/246,428 Office Action dated Aug. 26, 2014.
U.S. Appl. No. 13/246,428 Office Action dated Jan. 14, 2015.
U.S. Appl. No. 13/402,215 Office Action dated Mar. 19, 2013.
U.S. Appl. No. 13/529,172 Office action dated Sep. 24, 2013.
U.S. Appl. No. 13/612,768 Office Action dated Jul. 30, 2015.
U.S. Appl. No. 13/612,768 Office Action dated May 30, 2014.
U.S. Appl. No. 13/612,768 Office Action dated Nov. 17, 2014.
U.S. Appl. No. 13/612,768 Office Action dated Oct. 1, 2013.
U.S. Appl. No. 13/612,778 Office Action dated Apr. 28, 2014.
U.S. Appl. No. 13/612,778 Office Action dated Nov. 7, 2015.
U.S. Appl. No. 13/612,778 Office Action dated Nov. 7, 2014.
U.S. Appl. No. 13/634,863 Office Action dated Jan. 28, 2015.
U.S. Appl. No. 13/634,863 Office Action dated Sep. 8, 2015.
U.S. Appl. No. 13/794,368 Office Action dated May 8, 2015.
U.S. Appl. No. 13/794,368 Office Action dated Nov. 26, 2014.
U.S. Appl. No. 13/794,368 Office Action dated Sep. 23, 2015.
U.S. Appl. No. 13/801,780 Office Action dated Jun. 5, 2015.

(56) References Cited

OTHER PUBLICATIONS

U.S. Appl. No. 13/801,780 Office Action dated Nov. 14, 2014.
U.S. Appl. No. 13/968,313 Office Action dated Jun. 26, 2014.
U.S. Appl. No. 14/244,679 Office Action dated Oct. 23, 2015.
U.S. Appl. No. 14/295,226 Office Action dated May 7, 2015.
U.S. Appl. No. 14/295,226 Office Action dated Oct. 8, 2014.
U.S. Appl. No. 14/295,226 Office Action dated Sep. 9, 2015.
U.S. Appl. No. 14/447,412 Office Action dated Jul. 15, 2015.
U.S. Appl. No. 14/447,412 Office Action dated Mar. 3, 2015.
U.S. Appl. No. 14/530,499 Office Action dated May 14, 2015.
U.S. Appl. No. 14/678,392 Office Action dated Oct. 8, 2015.
U.S. Appl. No. 14/678,392 Office Action dated Sep. 24, 2015.
U.S. Appl. No. 14/796,910 Office Action dated Sep. 25, 2015,.
Wake Forest Baptist Medical Center (Wake Forest Physician Reports First Human Recipients of Laboratory-Grown Organs. 2006 pp. 1-2).
Wang et al. Bone marrow mesenchymal stem cells promote cell proliferation and neurotrophic function of Schwann cells in vitro and in vivo. Brain Research 1262:7-15 (2009).
Xu et al. A three-dimensional in vitro ovarian cancer coculture model using a high-throughput cell patterning platform. Biotechnology Journal 6(2):204-212 (2011).
Xu et al. In vivo generation of functional tissues using the inkjet printing technology. Tissue Engineering 13(7):1713-1714 (2007).
Yamauchi et al. A Three-Dimensional Cell Culture Model for Bovine Endometrium: Regeneration of a Multicellular Spheroid Using Ascorbate. Placenta 24:258-269 (2003).
Zhang et al. Characterization of printable cellular micro-fluidic channels for tissue engineering. Biofabrication 5:025004 (2013).
Henmi, C., et al., "Development of an effective three dimensional fabrication technique using inkjet technology for tissue model samples," *AATEX 14*:689-692, Japanese Society for Alternatives to Animal Experiments, Japan (2007).

\* cited by examiner

DEVICES, SYSTEMS, AND METHODS FOR THE FABRICATION OF TISSUE

CROSS-REFERENCE TO RELATED APPLICATIONS

This application is a continuation of U.S. application Ser. No. 14/950,567, filed Nov. 24, 2015, which is a continuation of U.S. application Ser. No. 14/530,499, filed Oct. 31, 2014, which is a continuation of U.S. application Ser. No. 13/968,313, filed Aug. 15, 2013, which is a continuation of U.S. application Ser. No. 13/246,428, filed Sep. 27, 2011, which claims the benefit of U.S. provisional App. Ser. No. 61/405,582, filed Oct. 21, 2010, each of which is incorporated by reference in its entirety.

BACKGROUND OF INVENTION

A number of pressing problems confront the healthcare industry. As of December 2009 there were 105,305 patients registered by United Network for Organ Sharing (UNOS) as needing an organ transplant. Between January and September 2009, only 21,423 transplants were performed. Each year more patients are added to the UNOS list than transplants are performed, resulting in a net increase in the number of patients waiting for a transplant. For example, at the beginning of 2008, 75,834 people were registered as needing a kidney; at the end of that year, the number had grown to 80,972. 16,546 kidney transplants were performed that year, but 33,005 new patients were added to the list. The 2008 transplant rate for a patient registered by UNOS as needing a kidney was 20%. The mortality rate of waitlist patients was 7%.

Additionally, the research and development cost of a new pharmaceutical compound is approximately $1.8 billion. See Paul, et al. (2010). How to improve R&D productivity: the pharmaceutical industry's grand challenge. Nature Reviews Drug Discovery 9(3):203-214. Drug discovery is the process by which drugs are discovered and/or designed. The process of drug discovery generally involves at least the steps of: identification of candidates, synthesis, characterization, screening, and assays for therapeutic efficacy. Despite advances in technology and understanding of biological systems, drug discovery is still a lengthy, expensive, and inefficient process with low rate of new therapeutic discovery.

SUMMARY OF THE INVENTION

There is a need for tools and techniques that facilitate application of regenerative medicine and tissue engineering technologies to relieving the urgent need for tissues and organs. There is also a need for tools and techniques that substantially increase the number and quality of innovative, cost-effective new medicines, without incurring unsustainable R&D costs. Accordingly, the inventors describe herein devices, systems, and methods for fabricating tissues and organs.

Described herein are bioprinters comprising: one or more printer heads, wherein a printer head comprises a means for receiving and holding at least one cartridge, and wherein said cartridge comprises contents selected from one or more of: bio-ink and support material; a means for calibrating the position of at least one cartridge; and a means for dispensing the contents of at least one cartridge. In one embodiment, a printer head described herein comprises a means for receiving and holding one cartridge. In another embodiment, a printer head described herein comprises a means for receiving and holding more than one cartridge. In another embodiment, the bioprinter further comprises a printer stage. In another embodiment, the means for receiving and holding at least one cartridge is selected from: magnetic attraction, a collet chuck grip, a ferrule, a nut, a barrel adaptor, or a combination thereof. In yet another embodiment, the means for receiving and holding at least one cartridge is a collet chuck grip. In yet another embodiment, the means for calibrating the position of at least one cartridge of is selected from: laser alignment, optical alignment, mechanical alignment, piezoelectric alignment, magnetic alignment, electrical field or capacitance alignment, ultrasound alignment, or a combination thereof. In yet another embodiment, the means for calibrating the position of at least one cartridge is laser alignment. In another embodiment, the means for dispensing the contents of at least one cartridge is application of a piston, application of pressure, application of compressed gas, hydraulics, or a combination thereof. In yet another embodiment, the means for dispensing the contents of at least one cartridge is application of a piston. In yet another embodiment, the diameter of the piston is less than the diameter of a cartridge. In another embodiment, the bioprinter further comprises a means for adjusting temperature. In yet another embodiment, the bioprinter further comprises a means for adjusting the ambient temperature, the temperature of a cartridge, the temperature of the contents of the cartridge, the temperature of the receiving surface, or a combination thereof. In yet another embodiment, the means for adjusting temperature is a heating element. In yet another embodiment, the means for adjusting temperature is a heater. In yet another embodiment, the means for adjusting temperature is a radiant heater, a convection heater, a conductive heater, a fan heater, a heat exchanger, or a combination thereof. In yet another embodiment, the means for adjusting temperature is a cooling element. In yet another embodiment, the means for adjusting temperature is a container of coolant, a chilled liquid, ice, a radiant cooler, a convection cooler, a conductive cooler, a fan cooler, or a combination thereof. In yet another embodiment, the temperature is adjusted to between about 40 and about 90° C. In yet another embodiment, the temperature is adjusted to between about 0 and about 10° C. In another embodiment, a bioprinter disclosed herein, further comprises a means for applying a wetting agent to one or more of: the printer stage; the receiving surface, the deposition orifice, bio-ink, support material, or the printed construct.

Also disclosed herein are methods of calibrating the position of a cartridge comprising a deposition orifice, wherein the cartridge is attached to a bioprinter, comprising: calibrating the position of the cartridge along at least one axis; wherein the axis is selected from the x-axis, y-axis, and z-axis; and wherein each calibration is made by use of a laser. In one embodiment, the methods comprise activating the laser and generating at least one substantially stable and/or substantially stationary laser beam, and where said laser beam is horizontal to the ground. In another embodiment, the methods comprise activating the laser and generating at least one substantially stable and/or substantially stationary laser beam, and where said laser beam is vertical to the ground. In yet another embodiment, each calibration is made by use of first and a second laser. In yet another embodiment, the first laser is vertical to the ground and the second laser is horizontal to the ground. In another embodiment, calibrating the position of the cartridge along the y-axis by use of a horizontal laser comprises: positioning the cartridge so that the cartridge is (i) located in a first y octant and (ii) the dispensing orifice is below the upper threshold of the laser beam; (a) moving the cartridge towards the laser beam and stopping said movement as soon as the laser beam is interrupted by the cartridge, wherein the position at which the laser beam is interrupted by the cartridge is the first y position; (b) re-positioning the cartridge so that the cartridge is located in the second y octant and the dispensing orifice is below the upper threshold of the laser beam; (c) moving the cartridge towards the laser beam and stopping said movement as soon as the laser beam is interrupted by the cartridge, wherein the position at which the laser beam is interrupted is the second y position; (d) and calculating the mid-point between the first y position and the second y position. In another embodiment, calibrating the position of the cartridge along the x-axis by use of a horizontal laser comprises: (a) positioning the cartridge (i) at the mid-point between the first y position and the second y position, and (ii) outside the sensor threshold of the laser; (b) moving the cartridge towards the sensor threshold and stopping said movement as soon as the cartridge contacts the sensor threshold; (c) wherein the position at which the cartridge contacts the sensor increased by half the cartridge width is the x position. In another embodiment, calibrating the position of the cartridge along the z-axis by use of a horizontal laser comprises: (a) positioning the cartridge so that the dispensing orifice is located above the laser beam; (b) moving the cartridge towards the laser beam and stopping said movement as soon as the laser beam is interrupted by the cartridge, wherein the position at which the laser beam is interrupted is the z position. In another embodiment, calibrating the position of the cartridge along the y-axis by use of a vertical laser comprises: (a) positioning the cartridge so that the cartridge is (i) located in a first y octant and (ii) the dispensing orifice is outside the sensor threshold of the laser beam; (b) moving the cartridge towards the laser beam and stopping said movement as soon as the laser beam is interrupted by the cartridge, wherein the position at which the laser beam is interrupted by the cartridge is the first y position; (c) re-positioning the cartridge so that the cartridge is located in the second y octant and the dispensing orifice is outside of the sensor threshold of the laser beam; (d) moving the cartridge towards the laser beam and stopping said movement as soon as the laser beam is interrupted by the cartridge, wherein the position at which the laser beam is interrupted is the second y position; (e) calculating the mid-point between the first y position and the second y position; and (f) optionally, repeating (a)-(e) and averaging calculated mid-points. In another embodiment, calibrating the position of the cartridge along the x-axis by use of a vertical laser comprises: (a) positioning the cartridge so that the cartridge is (i) located in a first x octant and (ii) the dispensing orifice is outside the sensor threshold of the laser beam; (b) moving the cartridge towards the laser beam and stopping said movement as soon as the laser beam is interrupted by the cartridge, wherein the position at which the laser beam is interrupted by the cartridge is the first x position; (c) re-positioning the cartridge so that the cartridge is located in the second x octant and the dispensing orifice is outside of the sensor threshold of the laser beam; (d) moving the cartridge towards the laser beam and stopping said movement as soon as the laser beam is interrupted by the cartridge, wherein the position at which the laser beam is interrupted is the second x position; (e) calculating the mid-point between the first x position and the second x position; and (f) optionally, repeating (a)-(e) and averaging calculated mid-points. In another embodiment, calibrating the position of the cartridge along the z-axis by use of a vertical laser comprises: (a) positioning the printer head so that the dispensing orifice is located above the laser beam and outside of the laser sensor range threshold; (b) moving the printer head along the z-axis the sensor threshold is reached; wherein, the z-position is the position at which the laser sensor threshold is reached; and optionally, repeating steps (a) and (b) and calculating average z-positions. In another embodiment, calibrating the position of the cartridge along the z-axis comprises: visually determining the position of the dispensing orifice.

Further described herein are systems for calibrating the position of a cartridge comprising a dispensing orifice, wherein the cartridge is attached to a bioprinter, said system comprising: a means for calibrating the position of the cartridge along at least one axis, and wherein the axis is selected from the y-axis, x-axis, and z-axis. In one embodiment, the means for calibrating the cartridge is laser alignment, optical alignment, mechanical alignment, piezoelectric alignment, magnetic alignment, electrical field or capacitance alignment, ultrasound alignment, or a combination thereof. In another embodiment, the means for calibrating the cartridge is laser alignment. In yet another embodiment, the laser alignment means comprises at least one laser, selected from a horizontal laser and a vertical laser. In yet another embodiment, the laser alignment means comprises a horizontal laser and a vertical laser. In yet another embodiment, the laser alignment means is accurate to ±40 μm on the vertical axis and ±20 μm on the horizontal axis.

Further described herein are methods for fabricating tissue constructs, comprising: a computer module receiving input of a visual representation of a desired tissue construct; a computer module generating a series of commands, wherein the commands are based on the visual representation and are readable by a bioprinter; a computer module providing the series of commands to a bioprinter, and the bioprinter depositing bio-ink and support material according to the commands to form a construct with a defined geometry. In some embodiments, a computer module comprises a display screen. In further embodiments, a computer module comprises a graphical user interface (GUI). In still further embodiments, a user defines the content of one or more objects to form a visual representation of a desired tissue construct using a GUI provided by the computer module. In one embodiment, the display screen consists essentially of a grid comprising a plurality of objects of substantially the same shape and substantially equal size. In yet another embodiment, each object is in the shape of a circle. In yet another embodiment, the user defines the content of one or more objects to form a visual representation of a desired tissue construct. In yet another embodiment, the user defined content of an object is selected from bio-ink or support material. In further embodiments, the display screen consists of three-dimensional rendering(s) that are input by the user electronically or manually, whereby the various components of the three-dimensional rendering can be adjusted in any suitable plane or vector prior to executing a bioprinting protocol on the bioprinter.

Further described herein are methods of attaching a cartridge to a bioprinter, comprising: (a) inserting the cartridge into a collet chuck, wherein the collet chuck is attached to a printer head of the bioprinter; and (b) adjusting the outer collar of the collet chuck; wherein the inserting and adjusting do not substantially alter the position of the printer head.

Further described herein are cartridges for use with the bioprinters described herein, comprising at least one orifice, wherein the edges of the orifice are smooth or substantially smooth. In one embodiment, the cartridge is a capillary tube or a micropipette. In another embodiment, the cartridge comprises a bio-ink. In yet another embodiment, the cartridge comprises a support material. In yet another embodiment, the orifice is circular or square. In yet another embodiment, the cartridge has an internal diameter of about 1 µm to about 1000 µm. In yet another embodiment, the cartridge has an internal diameter of about 500 µm. In yet another embodiment, the cartridge has a volume of about 1 µl to about 50 µl. In yet another embodiment, the cartridge has a volume of about 5 µl. In yet another embodiment, the cartridge is marked to indicate the composition of the bio-ink. In yet another embodiment, the cartridge is marked to indicate the composition of the support material. In some embodiments, the bio-ink and/or support material is primed. In further embodiments, the bio-ink is primed by extruding the bio-ink to the level of the dispensing orifice prior to initiating the bioprinter protocol. In further embodiments, the support material is primed by extruding the support material to the level of the dispensing orifice prior to initiating the bioprinter protocol.

Further described herein are systems for attaching a cartridge to a bioprinter, comprising: a means for receiving and securing a cartridge to a printer head of a bioprinter, wherein use of the means for receiving and securing the cartridge do not substantially alter the position of the printer head. In some embodiments, the means for receiving and securing the cartridge to a printer head is selected from: magnetic attraction, a collet chuck grip, a ferrule, a nut, a barrel adaptor, or a combination thereof. In one embodiment, in the means for receiving and securing the cartridge to a printer head is a collet.

Further described herein are receiving surfaces for receiving one or more structures dispensed from bioprinters. In one embodiment, the receiving surface is flat or substantially flat. In another embodiment, the receiving surface is smooth or substantially smooth. In yet another embodiment, the receiving surface is (a) flat or substantially flat and (b) smooth or substantially smooth or (c) defined or substantially defined. In another embodiment, the topography of the receiving surface is designed to accommodate or influence the size, shape, or texture, or geometry one or more dispensed structures. In yet another embodiment, the receiving surface comprises a solid material, a semi-solid material, or a combination thereof. In yet another embodiment, the receiving surface comprises glass, plastic, metal, a metal alloy, or a combination thereof. In yet another embodiment, the receiving surface comprises a gel. In yet another embodiment, the receiving surface resists adhesion of the one or more structures. In yet another embodiment, the receiving surface comprises polymerized NovoGel™.

DETAILED DESCRIPTION OF INVENTION

Figure 1:
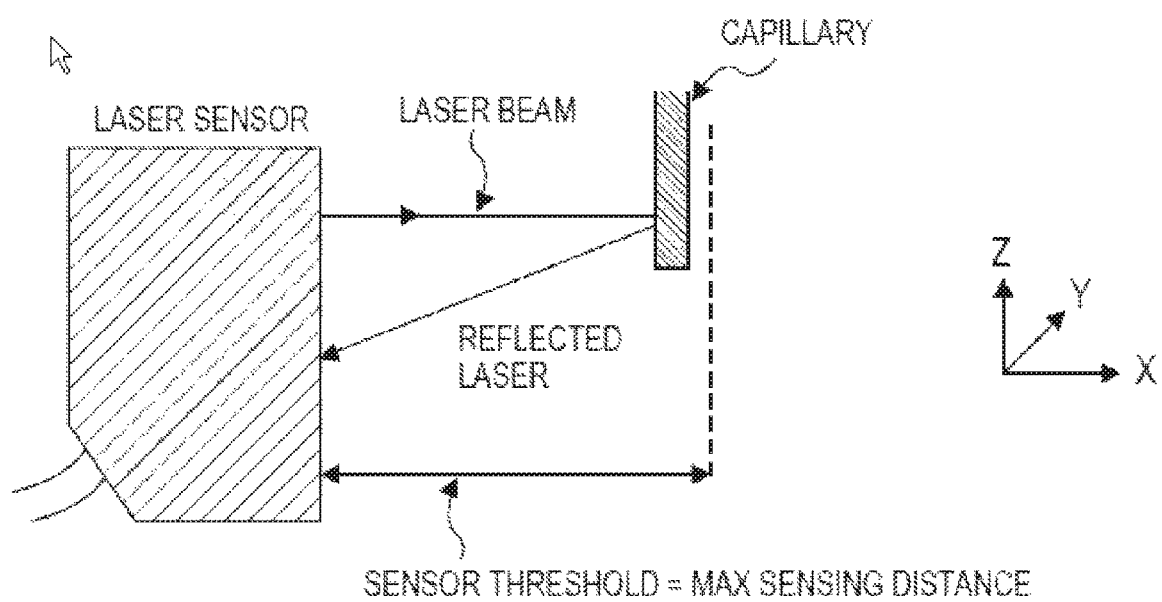
FIG. 1 illustrates a non-limiting example of calibration of a cartridge using a horizontal laser.

The invention relates to the fields of regenerative medicine, tissue/organ engineering, biologic and medical research, and drug discovery. More particularly, the invention relates to devices for fabricating tissues and organs, systems and methods for calibrating and using such devices, and tissues and organs fabricated by the devices, systems, and methods disclosed herein.

Disclosed herein, in certain embodiments, are bioprinters comprising: one or more printer heads, wherein a printer head comprises a means for receiving and holding at least one cartridge, and wherein said cartridge comprises contents selected from one or more of: bio-ink and support material; a means for calibrating the position of at least one cartridge; and a means for dispensing the contents of at least one cartridge.

Also disclosed herein, in certain embodiments, are methods of calibrating the position of a cartridge comprising a deposition orifice, wherein the cartridge is attached to a bioprinter, comprising: calibrating the position of the cartridge along at least one axis; wherein the axis is selected from the x-axis, y-axis, and z-axis; and wherein each calibration is made by use of a laser.

Also disclosed herein, in certain embodiments, are systems for calibrating the position of a cartridge comprising a deposition orifice, wherein the cartridge is attached to a bioprinter, said system comprising: a means for calibrating the position of the cartridge along at least one axis, wherein the axis is selected from the y-axis, x-axis, and z-axis.

Also disclosed herein, in certain embodiments, are methods for fabricating tissue constructs, comprising: a computer module receiving input of a visual representation of a desired tissue construct; a computer module generating a series of commands, wherein the commands are based on the visual representation and are readable by a bioprinter; a computer module providing the series of commands to a bioprinter; and the bioprinter depositing bio-ink and support material according to the commands to form a construct with a defined geometry.

Also disclosed herein, in certain embodiments, are methods of attaching a cartridge to a bioprinter, comprising: (a) inserting the cartridge into a collet chuck, wherein the collet chuck is attached to a printer head of the bioprinter; and (b) adjusting the outer collar of the collet chuck; wherein the inserting and adjusting do not substantially alter the position of the printer head.

Also disclosed herein, in certain embodiments, are systems for attaching a cartridge to a bioprinter, comprising: a means for receiving and securing a cartridge to a printer head of a bioprinter; wherein use of the means for receiving and securing the cartridge do not substantially alter the position of the printer head.

Certain Definitions

Unless otherwise defined, all technical and scientific terms used herein have the same meaning as commonly understood by one of ordinary skill in the art to which this invention belongs. All publications, patent applications, patents, and other references mentioned herein are incorporated by reference in their entirety.

As used in this specification and the appended claims, the singular forms "a," "an," and "the" include plural references unless the context clearly dictates otherwise. Thus, for example, references to "a nucleic acid" includes one or more nucleic acids, and/or compositions of the type described herein which will become apparent to those persons skilled in the art upon reading this disclosure and so forth. Any reference to "or" herein is intended to encompass "and/or" unless otherwise stated.

As used herein, "allograft" means an organ or tissue derived from a genetically non-identical member of the same species as the recipient.

As used herein, "bio-ink" means a liquid, semi-solid, or solid composition comprising a plurality of cells. In some embodiments, bio-ink comprises cell solutions, cell aggregates, cell-comprising gels, multicellular bodies, or tissues. In some embodiments, the bio-ink additionally comprises support material. In some embodiments, the bio-ink additionally comprises non-cellular materials that provide specific biomechanical properties that enable bioprinting.

As used herein, "bioprinting" means utilizing three-dimensional, precise deposition of cells (e.g., cell solutions, cell-containing gels, cell suspensions, cell concentrations, multicellular aggregates, multicellular bodies, etc.) via methodology that is compatible with an automated, computer-aided, three-dimensional prototyping device (e.g., a bioprinter).

As used herein, "cartridge" means any object that is capable of receiving (and holding) a bio-ink or a support material.

As used herein, a "computer module" means a software component (including a section of code) that interacts with a larger computer system. In some embodiments, a software module (or program module) comes in the form of a file and typically handles a specific task within a larger software system. In some embodiments, a module may be included in one or more software systems. In other embodiments, a module may be seamlessly integrated with one or more other modules into one or more software systems. A computer module is optionally a stand-alone section of code or, optionally, code that is not separately identifiable. A key feature of a computer module is that it allows an end user to use a computer to perform the identified functions.

As used herein, "implantable" means biocompatible and capable of being inserted or grafted into or affixed onto a living organism either temporarily or substantially permanently.

As used herein, "organ" means a collection of tissues joined into structural unit to serve a common function. Examples of organs include, but are not limited to, skin, sweat glands, sebaceous glands, mammary glands, bone, brain, hypothalamus, pituitary gland, pineal body, heart, blood vessels, larynx, trachea, bronchus, lung, lymphatic vessel, salivary glands, mucous glands, esophagus, stomach, gallbladder, liver, pancreas, small intestine, large intestine, colon, urethra, kidney, adrenal gland, conduit, ureter, bladder, fallopian tube, uterus, ovaries, testes, prostate, thyroid, parathyroid, meibomian gland, parotid gland, tonsil, adenoid, thymus, and spleen.

As used herein, "patient" means any individual. The term is interchangeable with "subject," "recipient," and "donor." None of the terms should be construed as requiring supervision (constant or otherwise) of a medical professional (e.g., physician, nurse, nurse practitioner, physician's assistant, orderly, hospice worker, social worker, clinical research associate, etc.) or a scientific researcher.

As used herein, "stem cell" means a cell that exhibits potency and self-renewal. Stem cells include, but are not limited to, totipotent cells, pluripotent cells, multipotent cells, oligopotent cells, unipotent cells, and progenitor cells. Stem cells may be embryonic stem cells, peri-natal stem cells, adult stem cells, amniotic stem cells, and induced pluripotent stem cells.

As used herein, "tissue" means an aggregate of cells. Examples of tissues include, but are not limited to, connective tissue (e.g., areolar connective tissue, dense connective tissue, elastic tissue, reticular connective tissue, and adipose tissue), muscle tissue (e.g., skeletal muscle, smooth muscle and cardiac muscle), genitourinary tissue, gastrointestinal tissue, pulmonary tissue, bone tissue, nervous tissue, and epithelial tissue (e.g., simple epithelium and stratified epithelium), endoderm-derived tissue, mesoderm-derived tissue, and ectoderm-derived tissue.

As used herein, "xenograft" means an organ or tissue derived from a different species as the recipient.

Current Methods of Organ Transplants

Currently, there is no reliable method for de novo organ synthesis. Organs are only derived from living donors (e.g., for kidney and liver donations), deceased donors (e.g., for lung and heart donations) and, in a few cases, animals (e.g., porcine heart valves). Thus, patients needing an organ transplant must wait for a donor organ to become available. This results in a shortage of available organs. Additionally, reliance on organs harvested from a living organism increases the chance of transplant rejection.

Transplant Rejections

In certain instances, a patient receiving an organ transplant experience hyperacute rejection. As used herein, "hyperacute rejection" means a complement-mediated immune response resulting from the recipient's having pre-existing antibodies to the donor organ. Hyperacute rejection occurs within minutes and is characterized by blood agglutination. If the transplanted organ is not immediately removed, the patient may become septic. Xenografts will produce hyperacute rejection unless the recipient is first administered immunosuppressants. In some embodiments, a tissue or organ fabricated de novo will not comprise any antigens and thus cannot be recognized by any antibodies of the recipient.

In certain instances, a patient receiving an organ transplant experiences acute rejection. As used herein, "acute rejection" means an immune response that begins about one week after transplantation to about one year after transplantation. Acute rejection results from the presence of foreign HLA molecules on the donor organ. In certain instances, APCs recognize the foreign HLAs and activate helper T cells. In certain instances, helper T cells activate cytotoxic T cells and macrophages. In certain instances, the presence of cytotoxic T cells and macrophages results in the death of cells with the foreign HLAs and thus damage (or death) of the transplanted organ. Acute rejection occurs in about 60-75% of kidney transplants, and 50-60% of liver transplants. In some embodiments, a tissue or organ fabricated de novo will not comprise any HLAs and thus will not result in the activation of helper T cells.

In certain instances, a patient receiving an organ transplant experiences chronic rejection. As used herein, "chronic rejection" means transplant rejection resulting from chronic inflammatory and immune responses against the transplanted tissue. In some embodiments, a tissue or organ fabricated de novo will not comprise any antigens or foreign HLAs and thus will not induce inflammatory or immune responses.

In certain instances, a patient receiving an organ transplant experiences chronic allograft vasculopathy (CAV). As used herein, "chronic allograft vasculopathy" means loss of function in transplanted organs resulting from fibrosis of the internal blood vessels of the transplanted organ. In certain instances, CAV is the result of long-term immune responses to a transplanted organ. In some embodiments, a tissue or organ fabricated de novo will not comprise any antigens or foreign HLAs and thus will not result in an immune response.

In order to avoid transplant rejection, organ recipients are administered immunosuppressant drugs. Immunosuppressants include, but are not limited to, corticosteroids (e.g., prednisone and hydrocortisone), calcineurin inhibitors (e.g., cyclosporine and tacrolimus), anti-proliferative agents (e.g., azathioprine and mycophenolic acid), antibodies against specific components of the immune system (e.g., basiliximab, dacluzimab, anti-thymocyte globulin (ATG) and anti-lymphocyte globulin (ALG) and mTOR inhibitors (e.g., sirolimus and everolimus)). However, immunosuppressants have several negative side-effects including, but not limited to, susceptibility to infection (e.g., infection by *Pneumocystis carinii* pneumonia (PCP), cytomegalovirus pneumonia (CMV), herpes simplex virus, and herpes zoster virus) and the spread of malignant cells, hypertension, dyslipidaemia, hyperglycemia, peptic ulcers, liver and kidney injury, and interactions with other medicines. In some embodiments, a tissue or organ fabricated de novo will not result in an immune response and thus will not require the administration of an immunosuppressant.

Infections

In certain instances, a donor organ may be infected with an infectious agent. Following the transplant of the infected organ, the infectious agent is able to spread throughout the donor (due in part to the use of immunosuppressant drugs). By way of non-limiting example, recipients have contracted HIV, West Nile Virus, rabies, hepatitis C, lymphocytic choriomeningitis virus (LCMV), tuberculosis, Chagas disease, and Creutzfeldt-Jakob disease from transplanted organs. While such infections are rare, they can nevertheless occur—social histories for deceased donors are often inaccurate as they are necessarily derived from next-of-kin, serological tests may produce false-negative results if seroconversion has not occurred, or serological tests may also produce false-negatives due to hemodilution following blood transfusion. Further, many uncommon infectious agents are not screened for due to the limited time a harvested organ is viable. In some embodiments, a tissue or organ fabricated de novo will not comprise any infectious agents.

Donor Complications

A living donor may also experience complications as a result of donating an organ. These complications include nosocomial infections, allergic reactions to the anesthesia, and surgical errors. Further, an organ donor may one day find themselves in need of the organ they donated. For example, the remaining kidney of a kidney donor or the remaining lobe of a liver donor may become damaged. In some embodiments, a tissue or organ fabricated de novo obviates the need for donor organs and thus will avoid negative side-effects to the donor.

In light of the shortage of available organs and all the complications that can follow a donor organ transplant, there is a need for a method of de novo fabrication of tissues and organs.

Tissue Engineering

Tissue engineering is an interdisciplinary field that applies and combines the principles of engineering and life sciences toward the development of biological substitutes that restore, maintain, or improve tissue function through augmentation, repair, or replacement of an organ or tissue. The basic approach to classical tissue engineering is to seed living cells into a biocompatible and eventually biodegradable environment (e.g., a scaffold), and then culture this construct in a bioreactor so that the initial cell population can expand further and mature to generate the target tissue upon implantation. With an appropriate scaffold that mimics the biological extracellular matrix (ECM), the developing tissue may adopt both the form and function of the desired organ after in vitro and in vivo maturation. However, achieving high enough cell density with a native tissue-like architecture is challenging due to the limited ability to control the distribution and spatial arrangement of the cells throughout the scaffold. These limitations may result in tissues or organs with poor mechanical properties and/or insufficient function. Additional challenges exist with regard to biodegradation of the scaffold, entrapment of residual polymer, and industrial scale-up of manufacturing processes. Scaffoldless approaches have been attempted. Current scaffoldless approaches are subject to several limitations:

Complex geometries, such as multi-layered structures wherein each layer comprises a different cell type, may require definitive, high-resolution placement of cell types within a specific architecture to reproducibly achieve a native tissue-like outcome.

Scale and geometry are limited by diffusion and/or the requirement for functional vascular networks for nutrient supply.

The viability of the tissues may be compromised by confinement material that limits diffusion and restricts the cells' access to nutrients.

Disclosed herein, in certain embodiments, are devices, systems, and methods that generate a three-dimensional tissue construct. The devices, systems, and methods disclosed herein utilize a three-phase process: (i) pre-processing, or bio-ink preparation, (ii) processing, i.e. the actual automated delivery/printing of the bio-ink particles into the bio-paper by the bioprinter, and (iii) post-processing, i.e., the maturation/incubation of the printed construct in the bioreactor. Final structure formation takes place during post-processing via the fusion of the bio-ink particles. The devices, systems, and methods disclosed herein have the following advantages:

They are capable of producing cell-comprising tissues and/or organs.

They mimic the environmental conditions of the natural tissue-forming processes by exploiting principles of developmental biology.

They can achieve a broad array of complex topologies (e.g., multilayered structures, repeating geometrical patterns, segments, sheets, tubes, sacs, etc.).

They are compatible with automated means of manufacturing and are scalable.

Bioprinting enables improved methods of generating cell-comprising implantable tissues that are useful in tissue repair, tissue augmentation, tissue replacement, and organ replacement. Additionally, bioprinting enables improved methods of generating micro-scale tissue analogs including those useful for in vitro assays.

Bioprinting

Disclosed herein, in certain embodiments, are devices, systems, and methods for fabricating tissues and organs. In some embodiments, the devices are bioprinters. In some embodiments, the methods comprise the use bioprinting techniques. In further embodiments, the tissues and organs fabricated by use of the devices, systems, and methods described herein are bioprinted.

In some embodiments, bioprinted cellular constructs, tissues, and organs are made with a method that utilizes a rapid prototyping technology based on three-dimensional, automated, computer-aided deposition of cells, including cell solutions, cell suspensions, cell-comprising gels or pastes, cell concentrations, multicellular bodies (e.g., cylinders, spheroids, ribbons, etc.), and support material onto a biocompatible surface (e.g., composed of hydrogel and/or a porous membrane) by a three-dimensional delivery device (e.g., a bioprinter). As used herein, in some embodiments, the term "engineered," when used to refer to tissues and/or organs means that cells, cell solutions, cell suspensions, cell-comprising gels or pastes, cell concentrates, multicellular aggregates, and layers thereof are positioned to form three-dimensional structures by a computer-aided device (e.g., a bioprinter) according to computer code. In further embodiments, the computer script is, for example, one or more computer programs, computer applications, or computer modules. In still further embodiments, three-dimensional tissue structures form through the post-printing fusion of cells or multicellular bodies similar to self-assembly phenomena in early morphogenesis.

While a number of methods are available to arrange cells, multicellular aggregates, and/or layers thereof on a biocompatible surface to produce a three-dimensional structure including manual placement, positioning by an automated, computer-aided machine such as a bioprinter is advantageous. Advantages of delivery of cells or multicellular bodies with this technology include rapid, accurate, and reproducible placement of cells or multicellular bodies to produce constructs exhibiting planned or pre-determined orientations or patterns of cells, multicellular aggregates and/or layers thereof with various compositions. Advantages also include assured high cell density, while minimizing cell damage.

In some embodiments, methods of bioprinting are continuous and/or substantially continuous. A non-limiting example of a continuous bioprinting method is to dispense bio-ink from a bioprinter via a dispense tip (e.g., a syringe, capillary tube, etc.) connected to a reservoir of bio-ink. In further non-limiting embodiments, a continuous bioprinting method is to dispense bio-ink in a repeating pattern of functional units. In various embodiments, a repeating functional unit has any suitable geometry, including, for example, circles, squares, rectangles, triangles, polygons, and irregular geometries. In further embodiments, a repeating pattern of bioprinted function units comprises a layer and a plurality of layers are bioprinted adjacently (e.g., stacked) to form an engineered tissue or organ. In various embodiments, 2, 3, 4, 5, 6, 7, 8, 9, 10, 11, 12, 13, 14, 15, or more layers are bioprinted adjacently (e.g., stacked) to form an engineered tissue or organ.

In some embodiments, a bioprinted functional unit repeats in a tessellated pattern. A "tessellated pattern" is a plane of figures that fills the plane with no overlaps and no gaps. An advantage of continuous and/or tessellated bioprinting can include an increased production of bioprinted tissue. Increased production can include achieving increased scale, increased complexity, or reduced time or cost of production. Another non-limiting potential advantage can be reducing the number of calibration events that are required to complete the bioprinting of a three-dimensional construct. Continuous bioprinting may also facilitate printing larger tissues from a large reservoir of bio-ink, optionally using a syringe mechanism.

Methods in continuous bioprinting may involve optimizing and/or balancing parameters such as print height, pump speed, robot speed, or combinations thereof independently or relative to each other. In one example, the bioprinter head speed for deposition was 3 mm/s, with a dispense height of 0.5 mm for the first layer and dispense height was increased 0.4 mm for each subsequent layer. In some embodiments, the dispense height is approximately equal to the diameter of the bioprinter dispense tip. Without limitation a suitable and/or optimal dispense distance does not result in material flattening or adhering to the dispensing needle. In various embodiments, the bioprinter dispense tip has an inner diameter of about, 20, 50, 100, 150, 200, 250, 300, 350, 400, 450, 500, 550, 600, 650, 700, 750, 800, 850, 900, 950, 1000 µm, or more, including increments therein. In various embodiments, the bio-ink reservoir of the bioprinter has a volume of about 0.5, 1, 2, 3, 4, 5, 6, 7, 8, 9, 10, 15, 20, 25, 30, 35, 40, 45, 50, 55, 60, 65, 70, 75, 80, 85, 90, 95, 100 cubic centimeters, or more, including increments therein. The pump speed may be suitable and/or optimal when the residual pressure build-up in the system is low. Favorable pump speeds may depend on the ratio between the cross-sectional areas of the reservoir and dispense needle with larger ratios requiring lower pump speeds. In some embodiments, a suitable and/or optimal print speed enables the deposition of a uniform line without affecting the mechanical integrity of the material.

The inventions disclosed herein include business methods. In some embodiments, the speed and scalability of the devices and methods disclosed herein are utilized to design, build, and operate industrial and/or commercial facilities for production of engineered tissues and/or organs. In further embodiments, the engineered tissues and/or organs are produced, stored, distributed, marketed, advertised, and sold as, for example, materials, tools, and kits for medical treatment of tissue damage, tissue disease, and/or organ failure or materials, tools, and kits to conduct biological assays and/or drug screening as a service.

Bioprinter

Disclosed herein, in certain embodiments, are bioprinters for fabricating tissues and organs. In some embodiments, a bioprinter is any instrument that automates a bioprinting process. In certain embodiments, a bioprinter disclosed herein comprises: one or more printer heads, wherein a printer head comprises a means for receiving and holding at least one cartridge, and wherein said cartridge comprises contents selected from one or more of: bio-ink and support material; a means for calibrating the position of at least one cartridge; and a means for dispensing the contents of at least one cartridge.

In various embodiments, a bioprinter dispenses bio-ink and/or support material in pre-determined geometrics (e.g., positions, patterns, etc.) in two or three dimensions. In some embodiments, a bioprinter achieves a particular geometry by moving a printer head relative to a printer stage or receiving surface adapted to receive bioprinted materials. In other embodiments, a bioprinter achieves a particular geometry by moving a printer stage or receiving surface relative to a printer head. In certain embodiments, the bioprinter is maintained in a sterile environment.

In some embodiments, a bioprinter disclosed herein comprises one or more printer heads. In further embodiments, a printer head comprises a means for receiving and holding at least one cartridge. In some embodiments, a printer head comprises a means for receiving and holding more than one cartridge. In some embodiments, the means for receiving and holding at least one cartridge is selected from: magnetic attraction, a collet chuck grip, a ferrule, a nut, a barrel adapter, or a combination thereof. In some embodiments, the means for receiving and holding at least one cartridge is a collet chuck grip.

In some embodiments, a bioprinter disclosed herein comprises a means for calibrating the position of at least one cartridge. In some embodiments, the means for calibrating the position of at least one cartridge of is selected from: laser alignment, optical alignment, mechanical alignment, piezoelectric alignment, magnetic alignment, electrical field or capacitance alignment, ultrasound alignment, or a combination thereof. In some embodiments, the means for calibrating the position of at least one cartridge is laser alignment.

In some embodiments, a bioprinter disclosed herein comprises a means for dispensing the contents of at least one cartridge. In some embodiments, the means for dispensing the contents of at least one cartridge is application of a piston, application of pressure, application of compressed gas, application of hydraulics, or application of a combination thereof. In some embodiments, the means for dispensing the contents of at least one cartridge is application of a piston. In some embodiments, the diameter of the piston is less than the diameter of a cartridge.

In some embodiments, a bioprinter disclosed herein further comprises a receiving surface. In further embodiments, a receiving surface is a non-cytotoxic surface onto which a bioprinter dispenses bio-ink and/or support material. In some embodiments, a bioprinter disclosed herein further comprises a printer stage. In further embodiments, a receiving surface is a surface of a printer stage. In other embodiments, a receiving surface is component separate from a printer stage, but is affixed to or supported by a stage. In some embodiments the receiving surface is flat or substantially flat. In some embodiments the surface is smooth or substantially smooth. In other embodiments, the surface is both substantially flat and substantially smooth. In still further embodiments the receiving surface is designed specifically to accommodate the shape, size, texture, or geometry of the bioprinted structure. In still further embodiments, the receiving surface controls or influences the size, shape, texture, or geometry of a bioprinted construct.

In some embodiments, a bioprinter disclosed herein further comprises a means for adjusting temperature. In some embodiments, the means for adjusting temperature adjusts and/or maintains the ambient temperature. In other various embodiments, the means for adjusting temperature adjusts and/or maintains the temperature of, by way of non-limiting example, the print head, cartridge, contents of the cartridge (e.g., bio-ink, support material, etc.), the printer stage, and the receiving surface.

In some embodiments, the means for adjusting temperature is a heating element. In some embodiments, the means for adjusting temperature is a heater. In some embodiments, the means for adjusting temperature is a radiant heater, a convection heater, a conductive heater, a fan heater, a heat exchanger, or a combination thereof. In some embodiments, the means for adjusting temperature is a cooling element. In some embodiments, the means for adjusting temperature is a container of coolant, a chilled liquid, ice, or a combination thereof. In some embodiments, the means for adjusting temperature is a radiant cooler, convection cooler, a conductive cooler, a fan cooler, or a combination thereof.

In various embodiments, the means for adjusting temperature adjusts a temperature to about 0, 5, 10, 15, 20, 25, 30, 35, 40, 45, 50, 55, 60, 65, 70, 75, 80, 85, or 90° C. including increments therein. In some embodiments, temperature is adjusted to between about 40° C. and about 90° C. In other embodiments, temperature is adjusted to between about 0° C. and about 10° C.

In some embodiments, a bioprinter disclosed herein, further comprises a means for applying a wetting agent to one or more of: the printer stage; the receiving surface, the deposition orifice, bio-ink, support material, or the printed construct. In some embodiments, the means for applying the wetting agent is any suitable method of applying a fluid (e.g., a sprayer, a pipette, an inkjet, etc.). In some embodiments, the wetting agent is water, tissue culture media, buffered salt solutions, serum, or a combination thereof. In further embodiments, a wetting agent is applied after the bio-ink or supporting material is dispensed by the bioprinter. In some embodiments, a wetting agent is applied simultaneously or substantially simultaneously with the bio-ink or supporting material being dispensed by the bioprinter. In some embodiments, a wetting agent is applied prior to the bio-ink or supporting material being dispensed by the bioprinter.

Printer Head

Disclosed herein, in certain embodiments, are bioprinters for fabricating tissues and organs. In some embodiments, a bioprinter disclosed herein comprises one or more printer heads. In further embodiments, a printer head comprises a means for receiving and holding at least one cartridge. In still further embodiments, a printer head attaches at least one cartridge to a bioprinter.

Many means for receiving and holding at least one cartridge are suitable. Suitable means for receiving and holding at least one cartridge include those that reliably, precisely, and securely attach at least one cartridge to a bioprinter. In various embodiments, the means for receiving and holding at least one cartridge is, by way of non-limiting example, magnetic attraction, a collet chuck grip, a ferrule, a nut, a barrel adapter, or a combination thereof.

In some embodiments, a printer head disclosed herein receives and holds one cartridge. In various other embodiments, a printer head disclosed herein receives and holds 2, 3, 4, 5, 6, 7, 8, 9, 10, or more cartridges simultaneously. In further embodiments, a printer head disclosed herein further comprises a means to select a cartridge to be employed in bioprinting from among a plurality of cartridges received and held.

In some embodiments, a printer head disclosed herein further comprises (or is in fluid communication with) a reservoir to contain bio-ink and/or support materials beyond the capacity of the one or more cartridges. In further embodiments, a reservoir supplies bio-ink and/or support materials to one or more cartridges for dispensing via a dispensing orifice. Printer head configurations including a reservoir are particularly useful in continuous or substantially continuous bioprinting applications. Many volumes are suitable for a reservoir disclosed herein. In various embodiments, a reservoir has an internal volume of, for example, 1, 2, 3, 4, 5, 6, 7, 8, 9, 10, 15, 20, 25, 30, 35, 40, 45, 50, 55, 60, 65, 70, 75, 80, 85, 90, 95, 100, 150, 200, 250, 300, 350, 400, 450, 500 ml or more, including increments therein.

In some embodiments, bioprinting involves using a computer to configure parameters such as print height, pump speed, robot speed, or combinations thereof independently or relative to each other. In further embodiments, computer code specifies the positioning of a printer head to configure printer head height above a receiving surface. In further embodiments, computer code specifies the direction and speed of the motion of a printer head to configure dispensing characteristics for bio-ink and/or support material.

Cartridges

Disclosed herein, in certain embodiments, are bioprinters for fabricating tissues and organs. In some embodiments, a cartridge attached to the bioprinter comprises bio-ink or support material. In some embodiments, the bioprinter dispenses bio-ink or support material in a specific pattern and at specific positions in order to form a specific cellular construct, tissue, or organ. In order to fabricate complex tissue constructs, the bioprinter deposits the bio-ink or support material at precise speeds and in uniform amounts. Thus, there is a need for a cartridge with (a) a dispensing orifice that is smooth or substantially smooth, and (b) an internal surface that is smooth or substantially smooth. As used herein, "cartridge" means any object that is capable of receiving (and holding) a bio-ink and/or support material.

In some embodiments, a cartridge disclosed herein comprises bio-ink. In some embodiments, a cartridge disclosed herein comprises support material. In some embodiments, a cartridge disclosed herein comprises a combination of bio-ink and support material.

Disclosed herein, in certain embodiments, are cartridges for use with a bioprinter disclosed herein, comprising at least one dispensing orifice. In some embodiments, a cartridge comprises one dispensing orifice. In various other embodiments, a cartridge comprises 2, 3, 4, 5, 6, 7, 8, 9, 10, 11, 12, 13, 14, 15, 20, 30, 40, 50, 60, 70, 80, 90, 100, or more dispensing orifices. In further embodiment, the edges of a dispensing orifice are smooth or substantially smooth.

Many shapes are suitable for the dispensing orifices disclosed herein. In various embodiments, suitable shapes for dispensing orifices include, by way of non-limiting examples, circular, ovoid, triangular, square, rectangular, polygonal, and irregular. In some embodiments, the orifice is circular. In other embodiments, the orifice is square. In yet other embodiments, the orifice is oval, oblong, or rectangular and dispenses solid or semi-solid bio-ink and/or support materials in a ribbon-like form.

In some embodiments, the internal surface of the cartridge is smooth or substantially smooth. In some embodiments, the cartridge is comprised of a rigid structure to facilitate calibration. In some embodiments, the walls of the cartridge are comprised of a material that resists attachment of cells. In some embodiments, the cartridges are comprised of a material that is biocompatible.

Many types of cartridges are suitable for use with bioprinters disclosed herein and the methods of using the same. In some embodiments, a cartridge is compatible with bioprinting that involves extruding a semi-solid or solid bio-ink or a support material through one or more dispensing orifices. In some embodiments, a cartridge is compatible with bioprinting that involves dispensing a liquid or semi-solid cell solution, cell suspension, or cell concentration through one or more dispensing orifices. In some embodiments, a cartridge is compatible with non-continuous bioprinting. In some embodiments, a cartridge is compatible with continuous and/or substantially continuous bioprinting.

In some embodiments, a cartridge is a capillary tube or a micropipette. In some embodiments, a cartridge is a syringe or a needle. Many internal diameters are suitable for substantially round or cylindrical cartridges. In various embodiments, suitable internal diameters include, by way of non-limiting examples, 1, 10, 50, 100, 200, 300, 400, 500, 600, 700, 800, 900, 1000 or more mm, including increments therein. In other various embodiments, suitable internal diameters include, by way of non-limiting examples, 1, 2, 3, 4, 5, 6, 7, 8, 9, 10, 20, 30, 40, 50, 60, 70, 80, 90, 100 or more mm, including increments therein. In some embodiments, a cartridge has an internal diameter of about 1 µm to about 1000 µm. In a particular embodiment, a cartridge has an internal diameter of about 500 µm. In another particular embodiment, a cartridge has an internal diameter of about 250 µm. Many internal volumes are suitable for the cartridges disclosed herein. In various embodiments, suitable internal volumes include, by way of non-limiting examples, 1, 10, 20, 30, 40, 50, 100, 200, 300, 400, 500, 600, 700, 800, 900, 1000 or more µl, including increments therein. In other various embodiments, suitable internal volumes include, by way of non-limiting examples, 1, 2, 3, 4, 5, 10, 20, 30, 40, 50, 60, 70, 80, 90, 100, 200, 300, 400, 500 or more ml, including increments therein. In some embodiments, a cartridge has a volume of about 1 µl to about 50 µl. In a particular embodiment, a cartridge has a volume of about 5 µl.

In some embodiments, a cartridge is compatible with ink-jet printing of bio-ink and/or support material onto a receiving surface such as that described in U.S. Pat. No. 7,051,654. In further embodiments, a cartridge includes dispensing orifices in the form of voltage-gated nozzles or needles under the control of the computer code described herein.

In some embodiments, the cartridge is primed. In some embodiments, priming the cartridge increases the accuracy of the dispensing, deposition, or extrusion process. As used herein, "primed" means the contents of the cartridge are made ready for dispensing, deposition, or extrusion by compacting and advancing the contents of the cartridge until the material to be dispensed (bio-ink or supporting material) is located in a position in contact with the dispensing orifice. In some embodiments, the cartridge is primed when the contents are compact or substantially compact, and the contents are in physical contact with the orifice of the cartridge.

In some embodiments, a cartridge is marked to indicate the composition of its contents. In further embodiments, a cartridge is marked to indicate the composition of a bio-ink and/or support material contained therein. In some embodiments, the surface of the cartridge is colored. In some embodiments, the outer surface of the cartridge is dyed, painted, marked with a pen, marked by a sticker, or a combination thereof.

In some embodiments, the outer surface of a cartridge is marked to increase the opacity of the surface of the cartridge (e.g., to increase the amount of a laser beam that is reflected off the surface of the cartridge). In some embodiments, the surface of a cartridge is colored. In some embodiments, the outer surface of a cartridge is scored. As used herein, "scored" means marking the surface of a cartridge to reduce the smoothness of the surface. Any suitable method is used to score the surface of a cartridge (e.g., application of an acidic substance, application of a caustic substance, application of an abrasive substance, etc.). In some embodiments, the outer surface of a cartridge is painted, polished (e.g., fire polished), etched (e.g., laser etched), marked with a pen, marked by a sticker, or a combination thereof.

Grip

Disclosed herein, in certain embodiments, are bioprinters for fabricating tissues and organs. In some embodiments, a cartridge attached to a bioprinter comprises bio-ink and/or support material. In some embodiments, the bioprinter dispenses the bio-ink and/or support material in a specific pattern and at specific positions in order to form a specific cellular construct, tissue, or organ. In some embodiments, a cartridge comprising bio-ink is disposable. In some embodiments, the cartridge is ejected from the bioprinter following extrusion of the contents. In some embodiments, a new cartridge is subsequently attached to the bioprinter.

In order to fabricate complex structures, the bioprinters disclosed herein dispense bio-ink and/or support material from a cartridge with a suitable repeatable accuracy. In various embodiments, suitable repeatable accuracies include those of about ±5, 10, 20, 30, 40, or 50 µm on any axis. In some embodiments, the bioprinters disclosed herein dispense bio-ink and/or support material from a cartridge with a repeatable accuracy of about ±20 µm. However, uncontrolled removal and insertion of cartridges can result in alterations of the position of the printer head (and thus the cartridges) with respect to the tissue construct, such that precision of the placement of the first bio-ink particle deposited from a new cartridge may vary relative to the last bio-ink particle deposited from the previous cartridge. Thus, there is a need for a method of attaching and securing a cartridge to a printer head, wherein said attaching and securing produce minimal alterations in the position of the printer head.

Disclosed herein, in certain embodiments, are methods of attaching a cartridge to a bioprinter, comprising: (a) inserting the cartridge into a collet chuck, wherein the collet chuck is attached to a printer head of the bioprinter, and (b) adjusting the outer collar of the collet chuck; wherein the inserting and adjusting do not substantially alter the position of the printer head.

Disclosed herein, in certain embodiments, are systems for attaching a cartridge to a bioprinter, comprising: a means for receiving and securing a cartridge to a printer head of a bioprinter; wherein use of the means for receiving and securing the cartridge do not substantially alter the position of the printer head. In some embodiments, the means for receiving and securing the cartridge to a printer head is a chuck or ferrule. As used herein, "chuck" means a holding device consisting of adjustable jaws. In some embodiments, the means for receiving and securing the cartridge to a printer head is a collet. As used herein, "collet" means a subtype of chuck—that forms a collar around the object to be held and exerts a strong clamping. As used herein, "ferrule" means a band (e.g., a metal band) used to secure one object to another. In some embodiments, the means for receiving and securing the cartridge to a printer head is a barrel adaptor. As used herein, "barrel adaptor" means a threaded tube used to secure one object to another.

Receiving Surface

Disclosed herein, in certain embodiments, are bioprinters for fabricating tissues and organs. In some embodiments, the bioprinter dispenses a plurality of elements, sections, and/or areas of bio-ink and/or support material onto a receiving surface. In further embodiments, dispensing occurs in a specific pattern and at specific positions. In still further embodiments, the locations at which the bioprinter deposits bio-ink and/or support material onto a receiving surface are defined by user input and translated into computer code.

In some embodiments, each of the elements, sections, and/or areas of bio-ink and/or support material has dimensions of less than 300 mm×300 mm×160 mm. By way of example only, the dimensions of a section of bio-ink or support material may be 75 mm×5.0 mm×5.0 mm; 0.3 mm×2.5 mm×2.5 mm; 1 mm×1 mm×50 mm; or 150 mm×150 mm×80 mm. Due to the generally small size of each section, and in some cases, the high degree of precision required, minute imperfections in the receiving surface may result in imperfections (and possibly, failure) of a cellular construct, tissue, or organ. Thus, there is a need for a substantially smooth and substantially flat receiving surface, or a defined or substantially defined receiving surface, that is able to receive sections of bio-ink and/or support material.

Disclosed herein, in certain embodiments, are receiving surfaces for receiving one or more structures generated by the bioprinter disclosed herein. In some embodiments, the receiving surface is flat or substantially flat. In some embodiments, the receiving surface is smooth or substantially smooth. In some embodiments, the receiving surface is flat or substantially flat. In some embodiments, the receiving surface is defined or substantially defined. In other embodiments the receiving surface is designed specifically to accommodate the shape, size, texture, or geometry of a specific bioprinted structure. In further embodiments, the receiving surface controls or influences the size, shape, texture, or geometry of a bioprinted construct.

In some embodiments, the receiving surface comprises a solid material, a semi-solid material, or a combination thereof. In some embodiments, the receiving surface comprises glass, coated glass, plastic, coated plastic, metal, a metal alloy, or a combination thereof. In some embodiments, the receiving surface comprises a gel. In some embodiments, the receiving surface and any coatings thereon are biocompatible. In various embodiments, the receiving surface comprises any of the support materials and/or confinement materials disclosed herein. In specific embodiments, the receiving surface comprises polymerized NovoGel™ or polymerized agarose, polymerized gelatin, extracellular matrix (or components thereof), collagen, or a combination thereof.

Software

Disclosed herein, in certain embodiments, are bioprinters for fabricating tissues and organs. In some embodiments, one or more cartridges attached to the bioprinter comprises bio-ink and/or support material. In some embodiments, the bioprinter dispenses bio-ink or support material in a specific pattern and at specific positions in order to form a specific cellular construct, tissue, or organ.

In order to fabricate complex tissue constructs, the bioprinter deposits the bio-ink or support material at precise locations (in two or three dimensions) on a receiving surface. In some embodiments, the locations at which the bioprinter deposits bio-ink and/or support material are defined by user input and translated into computer code. In further embodiments, the computer code includes a sequence of instructions, executable in the central processing unit (CPU) of a digital processing device, written to perform a specified task. In some embodiments, additional bioprinting parameters including, by way of non-limiting examples, print height, pump speed, robot speed, and/or control of variable dispensing orifices are defined by user input and translated into computer code. In other embodiments, such bioprinting parameters are not directly defined by user input, but are derived from other parameters and conditions by the computer code described herein.

Disclosed herein, in certain embodiments, are methods for fabricating tissue constructs, tissues, and organs, comprising: a computer module receiving input of a visual representation of a desired tissue construct; a computer module generating a series of commands, wherein the commands are based on the visual representation and are readable by a bioprinter, a computer module providing the series of commands to a bioprinter; and the bioprinter depositing bio-ink and/or support material according to the commands to form a construct with a defined geometry.

Computer Readable Medium

In some embodiments, the locations at which the bioprinter deposits the bio-ink and/or support material are defined by user input and translated into computer code. In some embodiments, the devices, systems, and methods disclosed herein further comprise computer readable media or media encoded with computer readable program code. In further embodiments, a computer readable medium is a tangible component of a digital processing device such as a bioprinter (or a component thereof) or a computer connected to a bioprinter (or a component thereof). In still further embodiments, a computer readable medium is optionally removable from a digital processing device. In some embodiments, a computer readable medium includes, by way of non-limiting examples, CD-ROMs, DVDs, flash memory devices, solid state memory, magnetic disk drives, magnetic tape drives, optical disk drives, cloud computing systems and services, and the like.

Computer Modules

In some embodiments, the devices, systems, and methods described herein comprise software, server, and database modules. In some embodiments, a "computer module" is a software component (including a section of code) that interacts with a larger computer system. In further embodiments, a software module (or program module) comes in the form of one or more files and typically handles a specific task within a larger software system.

In some embodiments, a module is included in one or more software systems. In other embodiments, a module is integrated with one or more other modules into one or more software systems. A computer module is optionally a stand-alone section of code or, optionally, code that is not separately identifiable. In some embodiments, the modules are in a single application. In other embodiments, the modules are in a plurality of applications. In some embodiments, the modules are hosted on one machine. In other embodiments, the modules are hosted on a plurality of machines. In some embodiments, the modules are hosted on a plurality of machines in one location. In other embodiments, the modules are hosted a plurality of machines in more than one location. Further described herein is the formatting of location and positioning data. In some embodiments, the data files described herein are formatted in any suitable data serialization format including, by way of non-limiting examples, tab-separated values, comma-separated values, character-separated values, delimiter-separated values, XML, JSON, BSON, and YAML. A key feature of a computer module is that it allows an end user to use a computer to perform the identified functions.

Graphic User Interface

In some embodiments, a computer module comprises a graphic user interface (GUI). As used herein, "graphic user interface" means a user environment that uses pictorial as well as textual representations of the input and output of applications and the hierarchical or other data structure in which information is stored. In some embodiments, a computer module comprises a display screen. In further embodiments, a computer module presents, via a display screen, a two-dimensional GUI. In other embodiments, a computer module presents, via a display screen, a three-dimensional GUI such as a virtual reality environment. In some embodiments, the display screen is a touchscreen or multitouch-screen and presents an interactive GUI.

In some embodiments, the display screen presents a GUI that consists essentially of a grid comprising regularly spaced objects of substantially the same shape and substantially equal size. The objects presented have any suitable shape. In some embodiments, suitable shapes for objects include, by way of non-limiting examples, circle, oval, square, rectangle, triangle, diamond, polygon, or a combination thereof.

In some embodiments, a user defines the content of one or more objects to form a two-dimensional or three-dimensional visual representation of a desired tissue construct. See, e.g., FIG. 4. In some embodiments, the user-defined content of an object is, by way of non-limiting examples, a bio-ink with various compositions or support material with various compositions. In some embodiments, the user defines the content of an object by modifying the color of the cell or the shape of the object.

Bio-Ink

Disclosed herein, in certain embodiments, are devices, systems, and methods for fabricating tissues and organs. In some embodiments, the devices comprise one or more printer heads for receiving and holding at least one cartridge that optionally contains bio-ink. In some embodiments, the methods comprise the use of bio-ink. In further embodiments, the tissues and organs fabricated by use of the devices, systems, and methods described herein comprise bio-ink at the time of fabrication or thereafter.

In some embodiments, "bio-ink" includes liquid, semi-solid, or solid compositions comprising a plurality of cells. In some embodiments, bio-ink comprises liquid or semi-solid cell solutions, cell suspensions, or cell concentrations. In further embodiments, a cell solution, suspension, or concentration comprises a liquid or semi-solid (e.g., viscous) carrier and a plurality of cells. In still further embodiments, the carrier is a suitable cell nutrient media, such as those described herein. In some embodiments, bio-ink comprises semi-solid or solid multicellular aggregates or multicellular bodies. In further embodiments, the bio-ink is produced by 1) mixing a plurality of cells or cell aggregates and a biocompatible liquid or gel in a pre-determined ratio to result in bio-ink, and 2) compacting the bio-ink to produce the bio-ink with a desired cell density and viscosity. In some embodiments, the compacting of the bio-ink is achieved by centrifugation, tangential flow filtration ("TFF"), or a combination thereof. In some embodiments, the compacting of the bio-ink results in a composition that is extrudable, allowing formation of multicellular aggregates or multicellular bodies. In some embodiments, "extrudable" means able to be shaped by forcing (e.g., under pressure) through a nozzle or orifice (e.g., one or more holes or tubes). In some embodiments, the compacting of the bio-ink results from growing the cells to a suitable density. The cell density necessary for the bio-ink will vary with the cells being used and the tissue or organ being produced. In some embodiments, the cells of the bio-ink are cohered and/or adhered. In some embodiments, "cohere," "cohered," and "cohesion" refer to cell-cell adhesion properties that bind cells, multicellular aggregates, multicellular bodies, and/or layers thereof. In further embodiments, the terms are used interchangeably with "fuse," "fused," and "fusion." In some embodiments, the bio-ink additionally comprises support material, cell culture medium, extracellular matrix (or components thereof), cell adhesion agents, cell death inhibitors, anti-apoptotic agents, anti-oxidants, extrusion compounds, and combinations thereof.

Cells

Disclosed herein, in various embodiments, are bio-inks that include liquid, semi-solid, or solid compositions comprising a plurality of cells. In some embodiments, bio-ink comprises liquid or semi-solid cell solutions, cell suspensions, or cell concentrations. In some embodiments, any mammalian cell is suitable for use in bio-ink and in the fabrication of tissues and organs using the devices, systems, and methods described herein. In various embodiments, the cells are any suitable cell. In further various embodiments, the cells are vertebrate cells, mammalian cells, human cells, or combinations thereof. In some embodiments, the type of cell used in a method disclosed herein depends on the type of cellular construct, tissue, or organ being produced. In some embodiments, the bio-ink comprises one type of cell (also referred to as a "homologous ink"). In some embodiments, the bio-ink comprises more than one type of cell (also referred to as a "heterologous ink").

In further embodiments, the cells are, by way of non-limiting examples, contractile or muscle cells (e.g., skeletal muscle cells, cardiomyocytes, smooth muscle cells, and myoblasts), connective tissue cells (e.g., bone cells, cartilage cells, fibroblasts, and cells differentiating into bone forming cells, chondrocytes, or lymph tissues), bone marrow cells, endothelial cells, skin cells, epithelial cells, breast cells, vascular cells, blood cells, lymph cells, neural cells, Schwann cells, gastrointestinal cells, liver cells, pancreatic cells, lung cells, tracheal cells, corneal cells, genitourinary cells, kidney cells, reproductive cells, adipose cells, parenchymal cells, pericytes, mesothelial cells, stromal cells, undifferentiated cells (e.g., embryonic cells, stem cells, and progenitor cells), endoderm-derived cells, mesoderm-derived cells, ectoderm-derived cells, and combinations thereof.

In some embodiments, the cells are adult, differentiated cells. In further embodiments, "differentiated cells" are cells with a tissue-specific phenotype consistent with, for example, a smooth muscle cell, a fibroblast, or an endothelial cell at the time of isolation, wherein tissue-specific phenotype (or the potential to display the phenotype) is maintained from the time of isolation to the time of use. In other embodiments, the cells are adult, non-differentiated cells. In further embodiments, "non-differentiated cells" are cells that do not have, or have lost, the definitive tissue-specific traits of for example, smooth muscle cells, fibroblasts, or endothelial cells. In some embodiments, non-differentiated cells include stem cells. In further embodiments, "stem cells" are cells that exhibit potency and self-renewal. Stem cells include, but are not limited to, totipotent cells, pluripotent cells, multipotent cells, oligopotent cells, unipotent cells, and progenitor cells. Stem cells may be embryonic stem cells, adult stem cells, amniotic stem cells, and induced pluripotent stem cells. In yet other embodiments, the cells are a mixture of adult, differentiated cells and adult, non-differentiated cells.

Cell Culture Media

In some embodiments, the bio-ink comprises a cell culture medium. The cell culture medium is any suitable medium. In various embodiments, suitable cell culture media include, by way of non-limiting examples, Dulbecco's Phosphate Buffered Saline, Earle's Balanced Salts, Hanks' Balanced Salts, Tyrode's Salts, Alsever's Solution, Gey's Balanced Salt Solution, Kreb's-Henseleit Buffer Modified, Kreb's-Ringer Bicarbonate Buffer, Puck's Saline, Dulbecco's Modified Eagle's Medium, Dulbecco's Modified Eagle's Medium/Nutrient F-12 Ham, Nutrient Mixture F-10 Ham (Ham's F-10), Medium 199, Minimum Essential Medium Eagle, RPMI-1640 Medium, Ames' Media, BGJb Medium (Fitton-Jackson Modification), Click's Medium, CMRL-1066 Medium, Fischer's Medium, Glascow Minimum Essential Medium (GMEM), Iscove's Modified Dulbecco's Medium (IMDM), L-15 Medium (Leibovitz), McCoy's 5A Modified Medium, NCTC Medium, Swim's S-77 Medium, Waymouth Medium, William's Medium E, or combinations thereof. In some embodiments, the cell culture medium is modified or supplemented. In some embodiments, the cell culture medium further comprises albumin, selenium, transferrins, fetuins, sugars, amino acids, vitamins, growth factors, cytokines, hormones, antibiotics, lipids, lipid carriers, cyclodextrins, or a combination thereof.

Extracellular Matrix

In some embodiments, the bio-ink further comprises one or more components of an extracellular matrix or derivatives thereof. In some embodiments, "extracellular matrix" includes proteins that are produced by cells and transported out of the cells into the extracellular space, where they may serve as a support to hold tissues together, to provide tensile strength, and/or to facilitate cell signaling. Examples, of extracellular matrix components include, but are not limited to, collagen, fibronectin, laminin, hyaluronates, elastin, and proteoglycans. For example, multicellular aggregates may contain various ECM proteins (e.g., gelatin, fibrinogen, fibrin, collagen, fibronectin, laminin, elastin, and/or proteoglycans). The ECM components or derivatives of ECM components can be added to the cell paste used to form the multicellular aggregate. The ECM components or derivatives of ECM components added to the cell paste can be purified from a human or animal source, or produced by recombinant methods known in the art. Alternatively, the ECM components or derivatives of ECM components can be naturally secreted by the cells in the elongate cellular body, or the cells used to make the elongate cellular body can be genetically manipulated by any suitable method known in the art to vary the expression level of one or more ECM components or derivatives of ECM components and/or one or more cell adhesion molecules or cell-substrate adhesion molecules (e.g., selectins, integrins, immunoglobulins, and adherins). The ECM components or derivatives of ECM components may promote cohesion of the cells in the multicellular aggregates. For example, gelatin and/or fibrinogen can suitably be added to the cell paste, which is used to form multicellular aggregates. The fibrinogen can then be converted to fibrin by the addition of thrombin.

In some embodiments, the bio-ink further comprises an agent that encourages cell adhesion.

In some embodiments, the bio-ink further comprises an agent that inhibits cell death (e.g., necrosis, apoptosis, or autophagocytosis). In some embodiments, the bio-ink further comprises an anti-apoptotic agent. Agents that inhibit cell death include, but are not limited to, small molecules, antibodies, peptides, peptibodies, or combination thereof. In some embodiments, the agent that inhibits cell death is selected from: anti-TNF agents, agents that inhibit the activity of an interleukin, agents that inhibit the activity of an interferon, agents that inhibit the activity of an GCSF (granulocyte colony-stimulating factor), agents that inhibit the activity of a macrophage inflammatory protein, agents that inhibit the activity of TGF-B (transforming growth factor B), agents that inhibit the activity of an MMP (matrix metalloproteinase), agents that inhibit the activity of a caspase, agents that inhibit the activity of the MAPK/JNK signaling cascade, agents that inhibit the activity of a Src kinase, agents that inhibit the activity of a JAK (Janus kinase), or a combination thereof. In some embodiments, the bio-ink comprises an anti-oxidant.

Extrusion Compounds

In some embodiments, the bio-ink further comprises an extrusion compound (i.e., a compound that modifies the extrusion properties of the bio-ink). Examples of extrusion compounds include, but are not limited to gels, hydrogels, surfactant polyols (e.g., Pluronic F-127 or PF-127), thermo-responsive polymers, hyaluronates, alginates, extracellular matrix components (and derivatives thereof), collagens, other biocompatible natural or synthetic polymers, nanofibers, and self-assembling nanofibers.

Gels, sometimes referred to as jellies, have been defined in various ways. For example, the United States Pharmacopoeia defines gels as semisolid systems consisting of either suspensions made up of small inorganic particles or large organic molecules interpenetrated by a liquid. Gels include a single-phase or a two-phase system. A single-phase gel consists of organic macromolecules distributed uniformly throughout a liquid in such a manner that no apparent boundaries exist between the dispersed macromolecules and the liquid. Some single-phase gels are prepared from synthetic macromolecules (e.g., carbomer) or from natural gums (e.g., tragacanth). In some embodiments, single-phase gels are generally aqueous, but will also be made using alcohols and oils. Two-phase gels consist of a network of small discrete particles.

Gels can also be classified as being hydrophobic or hydrophilic. In certain embodiments, the base of a hydrophobic gel consists of a liquid paraffin with polyethylene or fatty oils gelled with colloidal silica, or aluminum or zinc soaps. In contrast, the base of hydrophobic gels usually consists of water, glycerol, or propylene glycol gelled with a suitable gelling agent (e.g., tragacanth, starch, cellulose derivatives, carboxyvinylpolymers, and magnesium-aluminum silicates). In certain embodiments, the rheology of the compositions or devices disclosed herein is pseudo plastic, plastic, thixotropic, or dilatant.

Suitable hydrogels include those derived from collagen, hyaluronate, fibrin, alginate, agarose, chitosan, and combinations thereof. In other embodiments, suitable hydrogels are synthetic polymers. In further embodiments, suitable hydrogels include those derived from poly(acrylic acid) and derivatives thereof, poly(ethylene oxide) and copolymers thereof, poly(vinyl alcohol), polyphosphazene, and combinations thereof. In various specific embodiments, the support material is selected from: hydrogel, NovoGel™, agarose, alginate, gelatin, Matrigel™, hyaluronan, poloxamer, peptide hydrogel, poly(isopropyl n-polyacrylamide), polyethylene glycol diacrylate (PEG-DA), hydroxyethyl methacrylate, polydimethylsiloxane, polyacrylamide, poly(lactic acid), silicon, silk, or combinations thereof.

In some embodiments, hydrogel-based extrusion compounds are thermoreversible gels (also known as thermoresponsive gels or thermogels). In some embodiments, a suitable thermoreversible hydrogel is not a liquid at room temperature. In specific embodiments, the gelation temperature (Tgel) of a suitable hydrogel is about 10° C. about 15° C., about 20° C., about 25° C., about 30° C., about 35° C., and about 40° C., including increments therein. In certain embodiments, the Tgel of a suitable hydrogel is about 10° C. to about 25° C. In some embodiments, the bio-ink (e.g., comprising hydrogel, one or more cell types, and other additives, etc.) described herein is not a liquid at room temperature. In specific embodiments, the gelation temperature (Tgel) of a bio-ink described herein is about 10° C., about 15° C., about 20° C., about 25° C., about 30° C., about 35° C., and about 40° C., including increments therein. In certain embodiments, the Tgel of a bio-ink described herein is about 10° C. to about 25° C.

Polymers composed of polyoxypropylene and polyoxyethylene form thermoreversible gels when incorporated into aqueous solutions. These polymers have the ability to change from the liquid state to the gel state at temperatures that can be maintained in a bioprinter apparatus. The liquid state-to-gel state phase transition is dependent on the polymer concentration and the ingredients in the solution.

Poloxamer 407 (Pluronic F-127 or PF-127) is a nonionic surfactant composed of polyoxyethylene-polyoxypropylene copolymers. Other poloxamers include 188 (F-68 grade), 237 (F-87 grade), 338 (F-108 grade). Aqueous solutions of poloxamers are stable in the presence of acids, alkalis, and metal ions. PF-127 is a commercially available polyoxyethylene-polyoxypropylene triblock copolymer of general formula E106 P70 E106, with an average molar mass of 13,000. The polymer can be further purified by suitable methods that will enhance gelation properties of the polymer. It contains approximately 70% ethylene oxide, which accounts for its hydrophilicity. It is one of the series of poloxamer ABA block copolymers. PF-127 has good solubilizing capacity, low toxicity and is, therefore, considered a suitable extrusion compound.

In some embodiments, the viscosity of the hydrogels and bio-inks presented herein is measured by any means described. For example, in some embodiments, an LVDV-II+CP Cone Plate Viscometer and a Cone Spindle CPE-40 is used to calculate the viscosity of the hydrogels and bio-inks. In other embodiments, a Brookfield (spindle and cup) viscometer is used to calculate the viscosity of the hydrogels and bio-inks. In some embodiments, the viscosity ranges referred to herein are measured at room temperature. In other embodiments, the viscosity ranges referred to herein are measured at body temperature (e.g., at the average body temperature of a healthy human).

In further embodiments, the hydrogels and/or bio-inks are characterized by having a viscosity of between about 500 and 1,000,000 centipoise, between about 750 and 1,000,000 centipoise; between about 1000 and 1,000,000 centipoise; between about 1000 and 400,000 centipoise; between about 2000 and 100,000 centipoise; between about 3000 and 50,000 centipoise; between about 4000 and 25,000 centipoise; between about 5000 and 20,000 centipoise; or between about 6000 and 15,000 centipoise.

In some embodiments, the bio-ink comprises cells and extrusion compounds suitable for continuous bioprinting. In specific embodiments, the bio-ink has a viscosity of about 1500 mPa·s. A mixture of Pluronic F-127 and cellular material may be suitable for continuous bioprinting. Such a bio-ink may be prepared by dissolving Pluronic F-127 powder by continuous mixing in cold (4° C.) phosphate buffered saline (PBS) over 48 hours to 30% (w/v). Pluronic F-127 may also be dissolved in water. Cells may be cultivated and expanded using standard sterile cell culture techniques. The cells may be pelleted at 200 g for example, and re-suspended in the 30% Pluronic F-127 and aspirated into a reservoir affixed to a bioprinter where it can be allowed to solidify at a gelation temperature from about 10 to about 25° C. Gelation of the bio-ink prior to bioprinting is optional. The bio-ink, including bio-ink comprising Pluronic F-127 can be dispensed as a liquid.

In various embodiments, the concentration of Pluronic F-127 can be any value with suitable viscosity and/or cytotoxicity properties. A suitable concentration of Pluronic F-127 may also be able to support weight while retaining its shape when bioprinted. In some embodiments, the concentration of Pluronic F-127 is about 10%, about 15%, about 20%, about 25%, about 30%, about 35%, about 40%, about 45%, or about 50%. In some embodiments, the concentration of Pluronic F-127 is between about 30% and about 40%, or between about 30% and about 35%.

Figure 5:
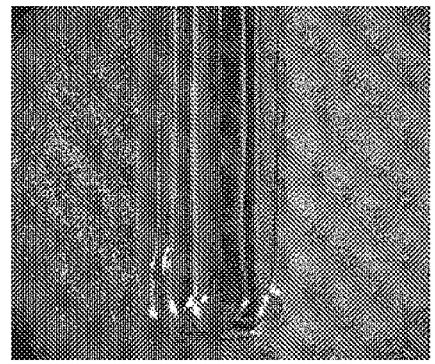
FIG. 5 illustrates a non-limiting example of a three-dimensional construct generated by continuous deposition of PF-127 using a NovoGen MMX™ bioprinter connected to a syringe with a 510 µm needle; in this case, a pyramid-shaped construct.

FIG. 5 depicts a three-dimensional, pyramid-shaped construct generated by continuous deposition of PF-127 using a NovoGen MMX™ bioprinter connected to a syringe with a 510 μm needle.

Figure 6:
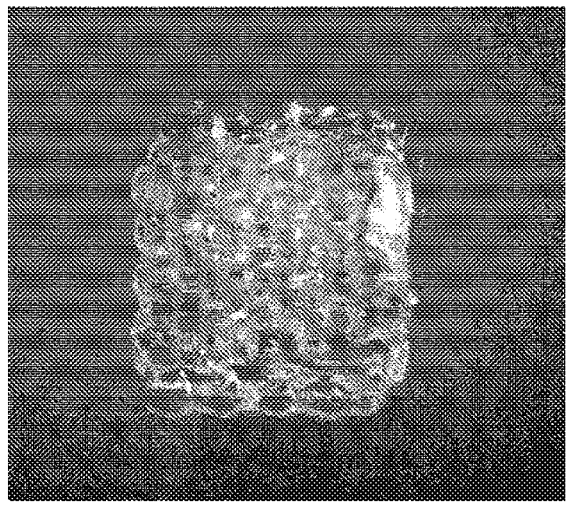
FIG. 6 illustrates a non-limiting example of a three-dimensional construct generated by continuous deposition of PF-127 using a NovoGen MMX™ bioprinter connected to a syringe with a 510 µm needle; in this case, cube-shaped (left) and hollow cube-shaped (right) constructs.
Figure 6:
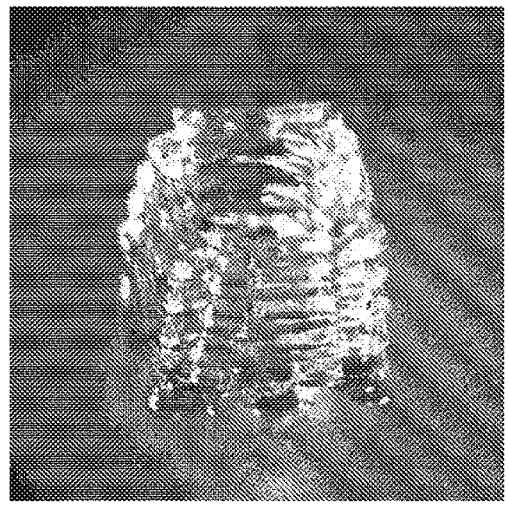

FIG. 6 depicts a three-dimensional, cube-shaped (left) and hollow cube-shaped (right) constructs generated by continuous deposition of PF-127 using a NovoGen MMX™ bioprinter connected to a syringe with a 510 μm needle.

In some embodiments, the non-cellular components of the bio-ink (e.g., extrusion compounds, etc.) are removed prior to use. In further embodiments, the non-cellular components are, for example, hydrogels, surfactant polyols, thermoresponsive polymers, hyaluronates, alginates, collagens, or other biocompatible natural or synthetic polymers. In still further embodiments, the non-cellular components are removed by physical, chemical, or enzymatic means. In some embodiments, a proportion of the non-cellular components remain associated with the cellular components at the time of use.

In some embodiments, the cells are pre-treated to increase cellular interaction. For example, cells may be incubated inside a centrifuge tube after centrifugation in order to enhance cell-cell interactions prior to shaping the bio-ink.

Support Material

Disclosed herein, in certain embodiments, are devices, systems, and methods for fabricating tissues and organs. In some embodiments, the devices comprise one or more printer heads for receiving and holding at least one cartridge that optionally contains support material. In some embodiments, the methods comprise the use of support material. In further embodiments, the tissues and organs fabricated by use of the devices, systems, and methods described herein comprise support material at the time of fabrication or thereafter.

In some embodiments, the support material is capable of excluding cells growing or migrating into or adhering to it. In some embodiments, the support material is permeable for nutrient media.

In some embodiments, the viscosity of the support material is changeable. In some embodiments, the viscosity of the support material is changed by modifying the temperature of the support material. In some embodiments, the viscosity of the support material is changed by modifying the pressure of the support material. In some embodiments, the viscosity of the support material is changed by modifying the concentration of the support material. In some embodiments, the viscosity of the support material is changed by crosslinking (e.g., by use of a chemical cross-linker), or photocrosslinking (e.g., using ultraviolet light exposure).

In some embodiments, the permeability of the support material is changeable. In some embodiments, the permeability of the support material is modified by varying the temperature of the support material or the temperature surrounding the support material. In some embodiments, the permeability of the support material is modified by contacting the support material with an agent that modifies permeability.

In some embodiments, the compliance (i.e., elasticity or hardness) of the support material is modified. In some embodiments, the compliance of the support material is modified by varying the temperature of the support material or the temperature surrounding the support material. In some embodiments, the compliance of the support material is modified by contacting the support material with an agent that modifies compliance.

Many support materials are suitable for use in the methods described herein. In some embodiments, hydrogels are exemplary support materials possessing one or more advantageous properties including: non-adherent, biocompatible, extrudable, bioprintable, non-cellular, and of suitable strength. In some embodiments, suitable hydrogels are natural polymers. In one embodiment, the confinement material is comprised of NovoGel™. In further embodiments, suitable hydrogels include those derived from surfactant polyols (e.g., Pluronic F-127), collagen, hyaluronate, fibrin, alginate, agarose, chitosan, derivatives or combinations thereof. In other embodiments, suitable hydrogels are synthetic polymers. In further embodiments, suitable hydrogels include those derived from poly(acrylic acid) and derivatives thereof, poly(ethylene oxide) and copolymers thereof, poly(vinyl alcohol), polyphosphazene, and combinations thereof. In various specific embodiments, the confinement material is selected from: hydrogel, NovoGel™, agarose, alginate, gelatin, Matrigel™, hyaluronan, poloxamer, peptide hydrogel, poly(isopropyl n-polyacrylamide), polyethylene glycol diacrylate (PEG-DA), hydroxyethyl methacrylate, polydimethylsiloxane, polyacrylamide, poly(lactic acid), silicon, silk, or combinations thereof.

In some embodiments, the support material contains cells prior to being present in the bioprinter. In some embodiments, the support material is a hydrogel containing a suspension of cells. In some embodiments, the support material is a hydrogel containing a mixture of more than one cell type.

Exemplary Uses of Support Materials

In some embodiments, the support material is used as building units for constructing a biological construct (e.g., cellular construct, tissue, organ, etc.). In further embodiments, the support material unit is used to define and maintain the domains void of cellular material (i.e., the intermediate cellular units) of a desired construct. In some embodiments, the support material is capable of assuming any shape or size.

For example, according to one embodiment, NovoGel™ solution (originally in powder phase mixed with buffer and water) may be heated to reduce its viscosity and taken up in a micropipette with a desired dimension (or in a chamber of a desired shape by negative displacement of a piston). The NovoGel™ solution in the pipette (or the chamber) may be cooled to room temperature, for example by forced air on the exterior of the pipette (or the chamber) or plunging the micropipette into a container with cold liquid, so that it can solidify into a gel with the desired shape, i.e., a support material. The resulting support material may be dispensed from the pipette or chamber during the construction of a particular cellular construct, tissue, or organ. See e.g., FIG. 4.

In some embodiments, the support material is used for increasing the viability of the engineered tissue or organ after bioprinting. In further embodiments, support material provides direct contact between the tissue or organ and a nutrient medium through a temporary or semi-permanent lattice of confinement material (e.g., support material). In some embodiments, the tissue is constrained in a porous or gapped material. Direct access of at least some of the cells of the tissue or organ to nutrients increases the viability of the tissue or organ.

In further embodiments, the methods disclosed herein comprise additional and optional steps for increasing the viability of an engineered tissue or organ including: 1) optionally dispensing base layer of confinement material (e.g., support material) prior to placing cohered multicellular aggregates; 2) optionally dispensing a perimeter of confinement material; 3) bioprinting cells of the tissue within a defined geometry; and 4) dispensing elongate bodies (e.g., cylinders, ribbons, etc.) of confinement material overlaying the nascent tissue in a pattern that introduces gaps in the confinement material, such as a lattice, mesh, or grid.

In some embodiments, the gaps overlaying pattern are distributed uniformly or substantially uniformly around the surface of the tissue or organ. In other embodiments, the gaps are distributed non-uniformly, whereby the cells of the tissue or organ are exposed to nutrients non-uniformly. In non-uniform embodiments, the differential access to nutrients may be exploited to influence one or more properties of the tissue or organ. For instance, it may be desirable to have cells on one surface of a bioprinted, cellular construct, tissue, or organ proliferate faster than cells on another surface. In some embodiments, the exposure of various parts of the tissue or organ to nutrients can be changed at various times to influence the development of the tissue or organ toward a desired endpoint.

In some embodiments, the confinement material is removed at any suitable time, including but not limited to, immediately after bioprinting (e.g., within 10 minutes), after bioprinting (e.g., after 10 minutes), before the cells are substantially cohered to each other, after the cells are substantially cohered to each other, before the cells produce an extracellular matrix, after the cells produce an extracellular matrix, just prior to use, and the like. In various embodiments, confinement material is removed by any suitable method. For example, in some embodiments, the confinement material is excised, pulled off the cells, digested, or dissolved.

Methods and Systems for Calibrating the Position of a Bioprinter Cartridge

Disclosed herein, in certain embodiments, are bioprinters for fabricating tissues and organs. In some embodiments, a cartridge attached to the bioprinter comprises a bio-ink and/or a support material. In some embodiments, the bioprinter deposits the bio-ink or support material in a specific pattern and at specific positions in order to form a specific tissue construct. In some embodiments, a cartridge comprising bio-ink is disposable. In some embodiments, the cartridge is ejected from the bioprinter following extrusion, dispensing, or deposition of the contents. In some embodiments, a new cartridge is attached to the bioprinter.

In order to fabricate complex structures, the bioprinters disclosed herein dispense bio-ink and/or support material from a cartridge with a suitable repeatable accuracy. In various embodiments, suitable repeatable accuracies include those of about ±5, 10, 20, 30, 40, or 50 µm on any axis. In some embodiments, the bioprinters disclosed herein dispense bio-ink and/or support material from a cartridge with a repeatable accuracy of about ±20 µm. However, in some embodiments, due to the removal and insertion of cartridges, the position of the printer head (and thus the cartridges) with respect to the tissue construct varies. Thus, there is a need for a method of precisely calibrating the position of the printer head, cartridge, and dispensing orifice with respect to the printer stage, receiving surface, tissue, or organ.

In some embodiments, the method of calibrating the position of a printer head comprises use of at least one laser. In further embodiments, the method of calibrating the position of a printer head comprises use of a first and second laser.

In some embodiments, the method of calibrating the position of a printer head comprises manual (e.g., visual) calibration.

In some embodiments, the method of calibrating the position of a printer head comprises manual calibration and laser calibration.

In some embodiments, the position of the printer head is calibrated along one axis, wherein the axis is selected from the x-axis, the y-axis, and the z-axis. In some embodiments, the position of the printer head is calibrated along two axes, wherein the axes are selected from the x-axis, the y-axis, and the z-axis. In some embodiments, the position of the printer head is calibrated along three axes, wherein the axes are selected from the x-axis, the y-axis, and the z-axis.

In some embodiments, calibration is made by use of at least one laser. In further embodiments, calibration is made by use of a first and a second laser.

Method for Calibrating Using a Horizontal Laser

Disclosed herein, in certain embodiments, are methods of calibrating the position of a printer head comprising a dispensing orifice. In some embodiments, a method disclosed herein further comprises activating a laser and generating at least one substantially stable and/or substantially stationary laser beam, and where said laser beam is horizontal to the ground. See FIG. 1.

In some embodiments, the methods comprise, calibrating the position of a printer head along at least one axis, wherein the axis is selected from the x-axis, y-axis, and z-axis. In some embodiments, the methods comprise calibrating the position of the printer head along at least two axes, wherein the axis is selected from the x-axis, y-axis, and z-axis. In some embodiments, the methods comprise calibrating the position of the printer head along at least three axes, wherein the axis is selected from the x-axis, y-axis, and z-axis. In some embodiments, the methods comprise (a) calibrating the position of the printer head along the y-axis; (b) calibrating the position of the printer head along the x-axis; and/or (c) calibrating the position of the printer head along the z-axis; wherein each axis corresponds to the axis of the same name in the Cartesian coordinate system. In some embodiments, calibration is made by use of at least one laser. In some embodiments, calibration is made by use of a first and a second laser.

In some embodiments, calibrating the position of a printer head along the y-axis comprises: (a) positioning the printer head so that the printer head is (i) located in a first y octant and (ii) the dispensing orifice is below the upper threshold of the laser beam; (b) moving the printer head towards the laser beam and stopping said movement as soon as the laser beam is interrupted by the printer head, wherein the position at which the laser beam is interrupted by the printer head is the first y position; (c) re-positioning the printer head so that the printer head is located in the second y octant and the dispensing orifice is below the upper threshold of the laser beam; (d) moving the printer head towards the laser beam and stopping said movement as soon as the laser beam is interrupted by the printer head, wherein the position at which the laser beam is interrupted is the second y position; (e) and calculating the mid-point between the first y position and the second y position.

In some embodiments, calibrating the position of a printer head along the x-axis comprises: (a) positioning the printer head (i) at the mid-point between the first y position and the second y position, and (ii) outside the sensor threshold of the laser; and (b) moving the printer head towards the sensor threshold and stopping said movement as soon as the printer head contacts the sensor threshold; wherein the position at which the printer head contacts the sensor increased by half the printer head width is the x position.

In some embodiments, calibrating the position of a printer head along the y-axis comprises: (a) positioning the printer head so that the laser beam can measure the precise location of one side of the printer head; (b) positioning the printer head so that the laser beam can measure the precise location of the opposing side of the printer head; (c) and calculating the midpoint location of the printer head to be relative to the laser location during each measurement and the measured distances.

In some embodiments, calibrating the position of a printer head along the x-axis comprises: (a) positioning the printer head so that the laser beam can measure the precise location of one side of the printer head; (b) positioning the printer head so that the laser beam can measure the precise location of the opposing side of the printer head; (c) and calculating the midpoint location of the printer head to be relative to the laser location during each measurement and the measured distances.

In some embodiments, calibrating the position of a printer head along the z-axis comprises: (a) positioning the printer head so that the dispensing orifice is located above the laser beam; and (b) moving the printer head towards the laser beam and stopping said movement as soon as the laser beam is interrupted by the printer head, wherein the position at which the laser beam is interrupted is the z position.

Method for Calibrating Using a Vertical Laser

Figure 2:
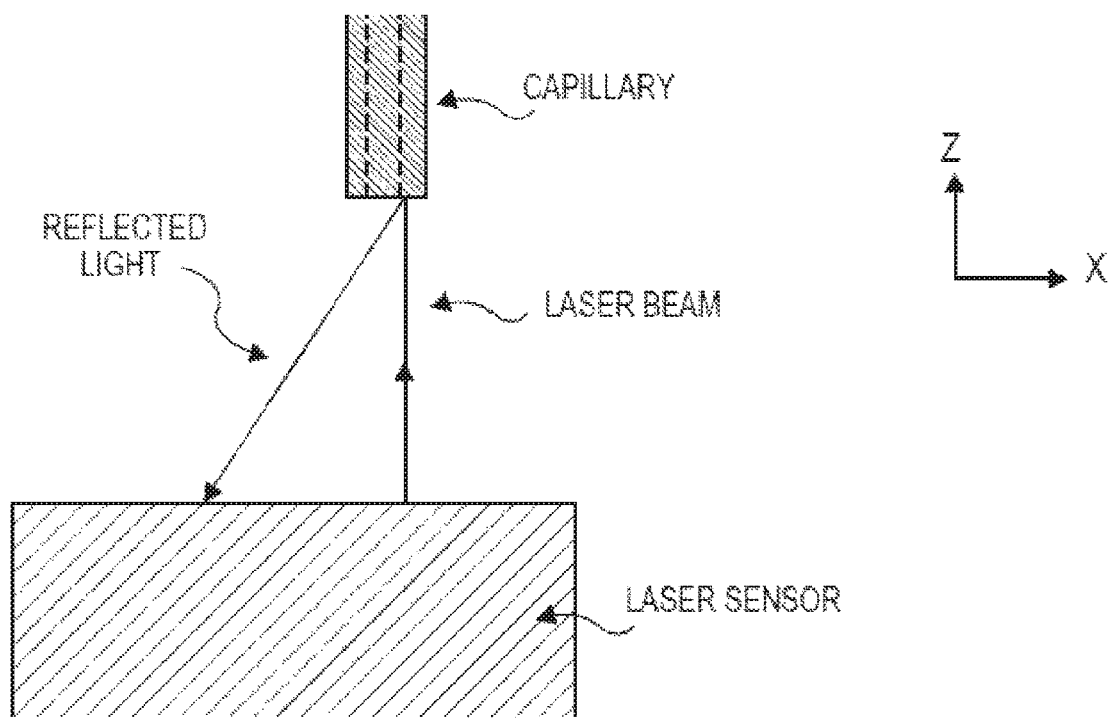
FIG. 2 illustrates a non-limiting example of calibration of a cartridge using a vertical laser.
Figure 3:
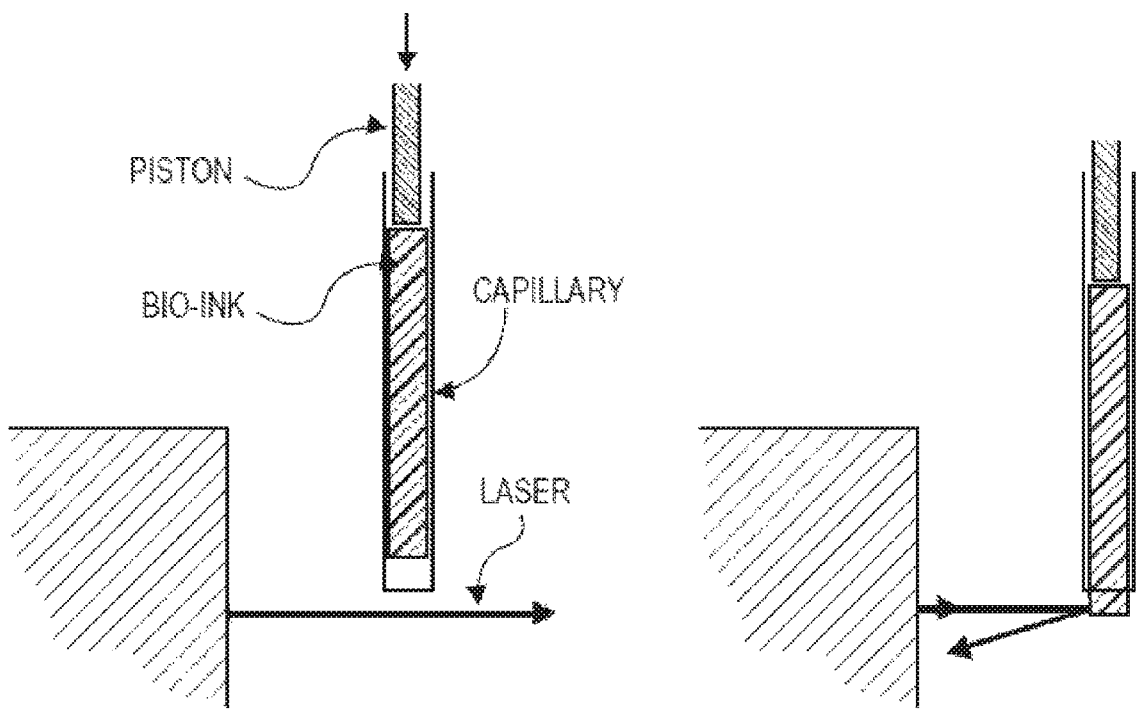
FIG. 3 illustrates a non-limiting example of a capillary priming process.

Disclosed herein, in certain embodiments, are methods of calibrating the position of a printer head comprising a dispensing orifice. In some embodiments, a method disclosed herein further comprises activating the laser and generating at least one substantially stable and/or substantially stationary laser beam, and where said laser beam is vertical to the ground. See FIG. 2.

In some embodiments, the methods comprise, calibrating the position of a printer head along at least one axis, wherein the axis is selected from the x-axis, y-axis, and z-axis. In some embodiments, the methods comprise calibrating the position of a printer head along at least two axes, wherein the axis is selected from the x-axis, y-axis, and z-axis. In some embodiments, the methods comprise calibrating the position of a printer head along at least three axes, wherein the axis is selected from the x-axis, y-axis, and z-axis.

In some embodiments, the methods comprise (a) calibrating the position of the printer head along the y-axis; (b) calibrating the position of the printer head along the x-axis; and (c) calibrating the position of the printer head along the z-axis; wherein each axis corresponds to the axis of the same name in the Cartesian coordinate system.

In some embodiments, calibrating the position of a printer head along the y-axis comprises: (a) positioning the printer head so that the printer head is (i) located in a first y octant and (ii) the dispensing orifice is outside the sensor threshold of the laser; (b) moving the printer head towards the laser beam and stopping said movement as soon as the laser beam is interrupted by the printer head, wherein the position at which the laser beam is interrupted by the printer head is the first y position; (c) re-positioning the printer head so that the printer head is located in the second y octant and the dispensing orifice is outside the sensor threshold of the laser; (d) moving the printer head towards the laser beam and stopping said movement as soon as the laser beam is interrupted by the printer head, wherein the position at which the laser beam is interrupted is the second y position; (e) and calculating the mid-point between the first y position and the second y position.

In some embodiments, calibrating the position of a printer head along the x-axis comprises: (a) positioning the printer head (i) at the mid-point between the first y position and the second y position, and (ii) outside the sensor threshold of the laser; and (b) moving the printer head towards the sensor threshold and stopping said movement as soon as the printer hbead contacts the sensor threshold; wherein the position at which the printer head contacts the sensor increased by half the printer head width is the x position.

In some embodiments, calibrating the position of a printer head along the z-axis comprises: (a) positioning the printer head so that the dispensing orifice is located above the laser beam so that it is just outside of the laser sensor range threshold; and (b) lowering the printer head until the sensor threshold is reached, wherein the position at which the laser sensor threshold is reached is the z position. In some embodiments, steps (a) and (b) are repeated at multiple points of the printer head and measured heights are averaged to determine the z position.

In some embodiments, calibrating the position of a printer head along the z-axis comprises: (a) positioning the printer head so that the laser beam can measure the precise location of one or more points on the bottom of the printer head; (b) calculating the absolute or average location of the printer head based on the laser position and known measured distance.

Method for Calibrating Using a Vertical and Horizontal Laser

Disclosed herein, in certain embodiments, are methods of calibrating the position of a printer head comprising a dispensing orifice, wherein the printer head is attached to a bioprinter, comprising calibrating the position of the printer head along at least one axis, wherein the axis is selected from the x-axis, y-axis, and z-axis. In some embodiments, the method comprises calibrating the position of a printer head along at least two axes, wherein the axis is selected from the x-axis, y-axis, and z-axis. In some embodiments, the method comprises calibrating the position of a printer head along at least three axes, wherein the axis is selected from the x-axis, y-axis, and z-axis.

In some embodiments, the methods comprise (a) calibrating the position of the printer head along the y-axis; (b) calibrating the position of the printer head along the x-axis; and (c) calibrating the position of the printer head along the z-axis, wherein each axis corresponds to the axis of the same name in the Cartesian coordinate system.

In some embodiments, calibration comprises use of a first laser and a second laser. In some embodiments, the first laser is a vertical laser and the second laser is a horizontal laser.

System for Calibrating Using a Laser

Disclosed herein, in certain embodiments, are systems for calibrating the position of a cartridge comprising a deposition orifice, wherein the cartridge is attached to a bioprinter, said system comprising: a means for calibrating the position of the cartridge along at least one axis, wherein the axis is selected from the y-axis, x-axis, and z-axis.

Also disclosed herein, in certain embodiments, are systems for calibrating the position of a printer head comprising a dispensing orifice, wherein the printer head is attached to a bioprinter, said system comprising: a means for calibrating the position of the printer head along an x-axis; a means for calibrating the position of the printer head along a y-axis; and a means for calibrating the position of the printer head along a z-axis.

In some embodiments, a system for calibrating the position of a printer head comprises a means for calibrating the printer head along the x-axis, y-axis, and z-axis. In some embodiments, the means for calibrating a printer head along the x-axis, y-axis, and z-axis is laser alignment, optical alignment, mechanical alignment, piezoelectric alignment, magnetic alignment, electrical field or capacitance alignment, ultrasound alignment, or a combination thereof.

In some embodiments, a system for calibrating the position of a printer head comprises a means for calibrating the printer head along the x-axis, y-axis, and z-axis. In some embodiments, the means for calibrating a printer head along the x-axis, y-axis, and z-axis is laser alignment. In some embodiments, the laser alignment means comprises at least one laser. In some embodiments, the laser alignment means comprises a plurality of lasers.

In some embodiments, the laser alignment means it has any suitable accuracy. In various embodiments, suitable accuracies include those of about ±5, 10, 20, 30, 40, or 50 μm on any axis. In some embodiments, the laser alignment means is accurate to ±40 μm on the vertical axis and ±20 μm on the horizontal axis.

In some embodiments, the laser path is uninterrupted between the laser source and the measurement point. In some embodiments, the laser path is altered by up to 179° by use of a reflective surface or optical lens. In some embodiments, the laser path is altered by 90°. In some embodiments, a horizontal laser beam is used to measure in a vertical path by deflection using a reflective surface. In some embodiments, a vertical laser beam is used to measure in a horizontal path by deflection using a reflective surface.

EXAMPLES

The following specific examples are to be construed as merely illustrative, and not limitative of the remainder of the disclosure in any way whatsoever. Without further elaboration, it is believed that one skilled in the art can, based on the description herein, utilize the present invention to its fullest extent. All publications cited herein are hereby incorporated by reference in their entirety. Reference thereto evidences the availability and public dissemination of such information.

Example 1: HASMC-HAEC Mixed Cellular Cylinders

Cell Culture
Smooth Muscle Cells:
Primary human aortic smooth muscle cells (HASMC) were maintained and expanded in low glucose Dulbecco's modified eagle medium (DMEM; Invitrogen Corp., Carlsbad, Calif.) supplemented with 10% fetal bovine serum (FBS), 100 U/ml Penicillin, 0.1 mg/ml streptomycin, 0.25 μg/ml of amphotericin B, 0.01M of HEPES (all from Invitrogen Corp., Carlsbad, Calif.), 50 mg/L of proline, 50 mg/L of glycine, 20 mg/L of alanine, 50 mg/L of ascorbic acid, and 3 μg/L of $CuSO_4$ (all from Sigma, St. Louis, Mo.) at 37° C. and 5% $CO_2$. Confluent cultures of HASMCs between passage 4 and 8 were used in all studies.
Endothelial Cells:
Primary human aortic endothelial cells (HAEC) were maintained and expanded in Medium 200 supplemented with 2% FBS, 1 μg/ml of hydrocortisone, 10 ng/ml of human epidermal growth factor, 3 ng/ml of basic fibroblast growth factor, 10 μg/ml of heparin, 100 U/ml Penicillin, 0.1 mg/ml streptomycin, and 0.25 μg/ml of amphotericin B (all from Invitrogen Corp., Carlsbad, Calif.). The cells were grown on gelatin (from porcine serum; Sigma, St. Louis, Mo.) coated tissue culture treated flasks at 37° C. and 5% $CO_2$. Confluent cultures of HAEC's between passage 4 and 8 were used in all studies.
NovoGel™ Mold
Preparation of 2% w/v NovoGel™ Solution:
1 g of low melting point NovoGel™ was dissolved in 50 ml of Dulbecco's phosphate buffered saline (DPBS). Briefly, the DPBS and NovoGel™ were heated to 85° C. on a hot plate with constant stirring until the NovoGel™ dissolved completely. NovoGel™ solution was sterilized by steam sterilization at 125° C. for 25 minutes. The NovoGel™ solution remained in liquid phase as long as the temperature is maintained above 66.5° C. Below this temperature a phase transition occurs, the viscosity of the NovoGel™ solution increases and the NovoGel™ forms a solid gel.
Preparation of NovoGel™ Mold:
A NovoGel™ mold was fabricated for the incubation of cellular cylinders using a Teflon® mold that fits a 10 cm Petri dish. Briefly, the Teflon® mold was pre-sterilized using 70% ethanol solution and subjecting the mold to UV light for 45 minutes. The sterilized mold was placed on top of the 10 cm Petri dish (VWR International LLC, West Chester, Pa.) and securely attached. This assembly (Teflon® mold+Petri dish) was maintained vertically and 45 ml of pre-warmed, sterile 2% NovoGel™ solution was poured in the space between the Teflon® mold and the Petri dish. The assembly was then placed horizontally at room temperature for 1 hour to allow complete gelation of the NovoGel™. After gelation, the Teflon® print was removed and the NovoGel™ mold was washed twice using DPBS. 17.5 ml of HASMC culture medium was then added to the NovoGel™ mold.
HASMC-HAEC Cylinders
Fabrication of HASMC-HAEC Mixed Cellular Cylinders:
To prepare mixed cellular cylinders HASMC and HAEC were individually collected and then mixed at pre-determined ratios. Briefly, the culture medium was removed from confluent culture flasks and the cells were washed with DPBS (1 ml/5 $cm^2$ of growth area). Cells were detached from the surface of the culture flasks by incubation in the presence of trypsin (1 ml/15 $cm^2$ of growth area) for 10 minutes. HASMC were detached using 0.15% trypsin while HAEC were detached using 0.1% trypsin. Following the incubation appropriate culture medium was added to the flasks (2× volume with respect to trypsin volume). The cell suspension was centrifuged at 200 g for 6 minutes followed by complete removal of supernatant solution. Cell pellets were resuspended in respective culture medium and counted using a hemacytometer. Appropriate volumes of HASMC and HAEC were combined to yield mixed cell suspensions containing 5, 7.5, 10, 12.5, and 15% HAEC (as a % of total cell population). The mixed cell suspensions were centrifuged at 200 g for 5 minutes followed by complete removal of supernatant solution. Mixed cell pellets were resuspended in 6 ml of HASMC culture medium and transferred to 20 ml glass vials, followed by incubation on an orbital shaker at 150 rpm for 60 minutes, and at 37° C. and 5% $CO_2$. This allows the cells to aggregate with one another and initiate cell-cell adhesions. Post-incubation, the cell suspension was transferred to a 15 ml centrifuge tube and centrifuged at 200 g for 5 minutes. After removal of the supernatant medium, the cell pellet was resuspended in 400 μl of HASMC culture medium and pipetted up and down several times to ensure all cell clusters were broken. The cell suspension was transferred into a 0.5 ml microfuge tube placed inside a 15 ml centrifuge tube followed by centrifugation at 2000 g for 4 minutes to form a highly dense and compact cell pellet. The supernatant medium was aspirated and the cells were transferred into capillary tubes (OD 1.0 mm, ID 0.5 mm, L 75 mm; Drummond Scientific Co., Broomall, Pa.) by aspiration so as to yield cell cylinders 50 mm in length. The cell paste inside the capillaries was incubated in HASMC medium for 20 minutes at 37° C. and 5% $CO_2$. The cellular cylinders were then deposited from the capillary tubes into the grooves of the NovoGel™ mold (covered with HASMC medium) using the plunger supplied with the capillaries. The cellular cylinders were incubated for 24 and 48 hours at 37° C. and 5% $CO_2$.

Example 2: Multi-Layered Vascular Tubes

Cell Culture
  Smooth Muscle Cells:
  Primary human aortic smooth muscle cells (HASMC; GIBCO) were maintained and expanded in low glucose Dulbecco's modified eagle medium (DMEM) supplemented with 10% fetal bovine serum (FBS), 100 U/ml Penicillin, 0.1 mg/ml streptomycin, 0.25 µg/ml of amphotericin B, 0.01M of HEPES (all from Invitrogen Corp., Carlsbad, Calif.), 50 mg/L of proline, 50 mg/L of glycine, 20 mg/L of alanine, 50 mg/L of ascorbic acid, and 3 µg/L of $CuSO_4$ (all from Sigma, St. Louis, Mo.) at 37° C. and 5% $CO_2$. Confluent cultures of HASMC between passage 4 and 8 were used in all studies.
  Endothelial Cells:
  Primary human aortic endothelial cells (HAEC) were maintained and expanded in Medium 200 supplemented with 2% FBS, 1 µg/ml of hydrocortisone, 10 ng/ml of human epidermal growth factor, 3 ng/ml of basic fibroblast growth factor, 10 µg/ml of heparin, 100 U/ml Penicillin, 0.1 mg/ml streptomycin, and 0.25 µg/ml of amphotericin B (all from Invitrogen Corp., Carlsbad, Calif.). The cells were grown on gelatin (from porcine serum) coated tissue culture treated flasks at 37° C. and 5% $CO_2$. Confluent cultures of HAEC between passage 4 and 8 were used in all studies.
  Fibroblasts:
  Primary human dermal fibroblasts (HDF) were maintained and expanded in Medium 106 supplemented with 2% FBS, 1 µg/ml of hydrocortisone, 10 ng/ml of human epidermal growth factor, 3 ng/ml of basic fibroblast growth factor, 10 µg/ml of heparin, 100 U/ml Penicillin, and 0.1 mg/ml streptomycin (all from Invitrogen Corp., Carlsbad, Calif.) at 37° C. and 5% $CO_2$. Confluent cultures of HDF between passage 4 and 8 were used in all studies.
NovoGel™ Solutions and Mold
  Preparation of 2% and 4% (w/v) NovoGel™ Solution:
  1 g or 2 g (for 2% or 4% respectively) of low melting point NovoGel™ (Ultrapure LMP) was dissolved in 50 ml of Dulbecco's phosphate buffered saline (DPBS). Briefly, the DPBS and NovoGel™ were heated to 85° C. on a hot plate with constant stirring until the NovoGel™ dissolves completely. NovoGel™ solution was sterilized by steam sterilization at 125° C. for 25 minutes. The NovoGel™ solution remains in liquid phase as long as the temperature is maintained above 66.5° C. Below this temperature a phase transition occurs, the viscosity of the NovoGel™ solution increases and the NovoGel™ forms a solid gel.
  Preparation of NovoGel™ Mold:
  A NovoGel™ mold was fabricated for the incubation of cellular cylinders using a Teflon® mold that fit a 10 cm Petri dish. Briefly, the Teflon® mold was pre-sterilized using 70% ethanol solution and subjecting the mold to UV light for 45 minutes. The sterilized mold was placed on top of the 10 cm Petri dish and securely attached. This assembly (Teflon® mold+Petri dish) was maintained vertically and 45 ml of pre-warmed, sterile 2% NovoGel™ solution was poured in the space between the Teflon® mold and the Petri dish. The assembly was then placed horizontally at room temperature for 1 hour to allow complete gelation of the NovoGel™. After gelation, the Teflon® print was removed and the NovoGel™ mold was washed twice using DPBS. Then, either 17.5 ml of HASMC culture medium was added to the NovoGel™ mold for incubating HASMC-HAEC mixed cell cylinders or 17.5 ml of HDF culture medium is added to the NovoGel™ mold for incubating HDF cell cylinders.
Cellular Cylinders
  Fabrication of HASMC-HAEC Mixed Cellular Cylinders:
  To prepare mixed cellular cylinders HASMC and HAEC were individually collected and then mixed at pre-determined ratios. Briefly, the culture medium was removed from confluent culture flasks and the cells were washed with DPBS (1 ml/5 $cm^2$ of growth area). Cells were detached from the surface of the culture flasks by incubation in the presence of trypsin (1 ml/15 $cm^2$ of growth area) for 10 minutes. HASMC were detached using 0.15% trypsin while HAEC were detached using 0.1% trypsin. Following the incubation appropriate culture medium was added to the flasks (2× volume with respect to trypsin volume). The cell suspension was centrifuged at 200 g for 6 minutes followed by complete removal of supernatant solution. Cell pellets were resuspended in respective culture medium and counted using a hemacytometer. Appropriate volumes of HASMC and HAEC were combined to yield a mixed cell suspension containing 15% HAEC and remainder 85% HASMC (as a percentage of total cell population). The mixed cell suspension was centrifuged at 200 g for 5 minutes followed by complete removal of supernatant solution. Mixed cell pellets were resuspended in 6 ml of HASMC culture medium and transferred to 20 ml glass vials, followed by incubation on an orbital shaker at 150 rpm for 60 minutes, and at 37° C. and 5% $CO_2$. This allows the cells to aggregate with one another and initiate cell-cell adhesions. Post-incubation, the cell suspension was transferred to a 15 ml centrifuge tube and centrifuged at 200 g for 5 mins. After removal of the supernatant medium, the cell pellet was resuspended in 400 µl of HASMC culture medium and pipetted up and down several times to ensure all cell clusters were broken. The cell suspension was transferred into a 0.5 ml microfuge tube placed inside a 15 ml centrifuge tube followed by centrifugation at 2000 g for 4 minutes to form a highly dense and compact cell pellet. The supernatant medium was aspirated and the cells were transferred into capillary tubes (OD 1.0 mm, ID 0.5 mm, L 75 mm) by aspiration so as to yield cell cylinders 50 mm in length. The cell paste inside the capillaries was incubated in HASMC medium for 20 minutes at 37° C. and 5% $CO_2$. The cellular cylinders were then deposited from the capillary tubes into the grooves of the NovoGel™ mold (covered with HASMC medium) using the plunger supplied with the capillaries. The cellular cylinders were incubated for 24 hours at 37° C. and 5% $CO_2$.
  Fabrication of HDF Cell Cylinders:
  HDF cylinders were prepared using a method similar to preparing HASMC-HAEC mixed cellular cylinders. Briefly, the culture medium was removed from confluent HDF culture flasks and the cells were washed with DPBS (1 ml/5 $cm^2$ of growth area). Cells were detached from the surface of the culture flasks by incubation in the presence of trypsin (0.1%; 1 mL/5 cm² of growth area) for 10 minutes. Following the incubation HDF culture medium was added to the flasks (2× volume with respect to trypsin volume). The cell suspension was centrifuged at 200 g for 6 minutes followed by complete removal of supernatant solution. Cell pellets were resuspended in 6 ml of HDF culture medium and transferred to 20 ml glass vials, followed by incubation on an orbital shaker at 150 rpm for 75 minutes, and at 37° C. and 5% $CO_2$. Post-incubation, the cell suspension was transferred to a 15 ml centrifuge tube and centrifuged at 200 g for 5 minutes. After removal of the supernatant medium, the cell pellet was resuspended in 400 µl of HDF culture medium and pipetted up and down several times to ensure all cell clusters were broken. The cell suspension was transferred into a 0.5 ml microfuge tube placed inside a 15 ml centrifuge tube followed by centrifugation at 2000 g for 4 minutes to form a highly dense and compact cell pellet. The supernatant medium was aspirated and the cells were transferred into capillary tubes (OD 1.0 mm, ID 0.5 mm, L 75 mm) by aspiration so as to yield cell cylinders 50 mm in length. The cell paste inside the capillaries were incubated in HDF culture medium for 20 minutes at 37° C. and 5% $CO_2$. The cellular cylinders were then deposited from the capillary tubes into the grooves of the NovoGel™ mold (covered with HDF medium). The cellular cylinders were incubated for 24 hours at 37° C. and 5% $CO_2$.

Fabrication of Multi-Layered Vascular Tubes

Preparation of NovoGel™ Base Plate:

A NovoGel™ base plate was fabricated by dispensing 10 ml of pre-warmed (>40° C.) NovoGel™ (2% w/v) into a 10 cm Petri dish. Immediately after dispensing, the NovoGel™ was evenly spread so as to cover the entire base of the dish and form a uniform layer. The Petri dish was incubated at room temperature for 20 minutes to allow the NovoGel™ to gel completely.

Figure 4:
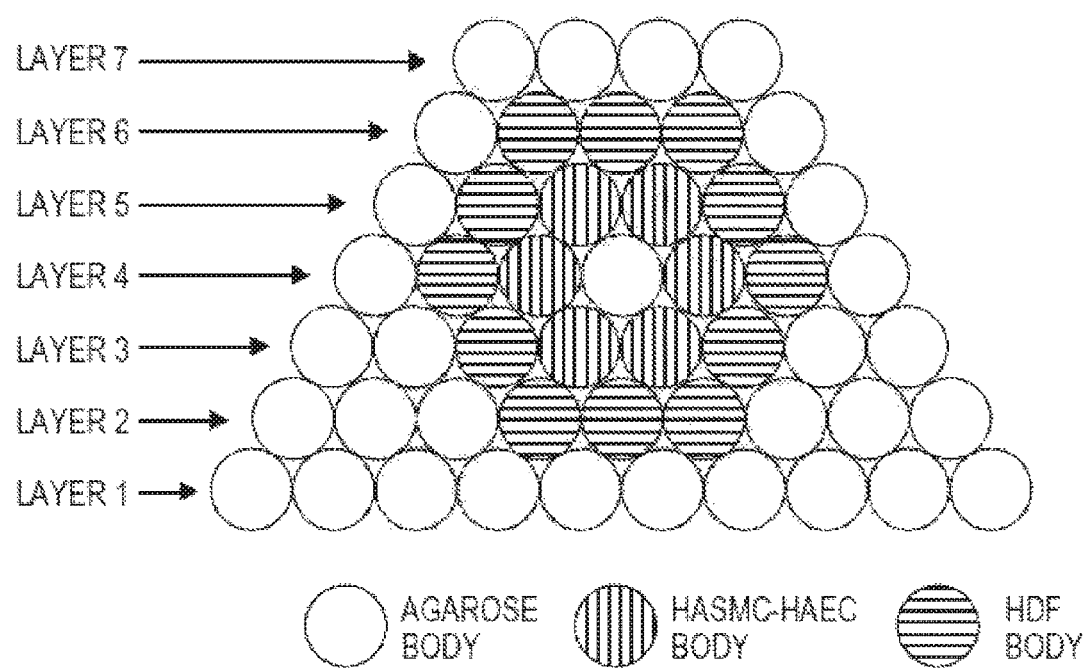
FIG. 4 illustrates a non-limiting example of a two-dimensional representation of a bioprinted tissue construct.

Multi-Layered Vascular Tube:

Vascular tubes consisting of an outer layer of HDF and an inner layer of HASMC-HAEC were fabricated utilizing HDF cylinders, and HASMC-HAEC mixed cell cylinders. A geometrical arrangement as shown in FIG. 4 was utilized. Briefly, at the end of the 24-hour incubation period mature HDF and HASMC-HAEC cylinders were aspirated back into the capillary tubes and placed in appropriate culture medium until further use. The support structure consisting of NovoGel™ rods was prepared as follows: Pre-warmed 2% NovoGel™ was aspirated into the capillary tubes (L=50 mm) and rapidly cooled in cold PBS solution (4° C.). The 5 cm long gelled NovoGel™ cylinder was deposited from the capillary (using the plunger) and laid down straight on the NovoGel™ base plate. A second NovoGel™ cylinder was adjoined to the first one and the process was repeated until 10 NovoGel™ cylinders were deposited to form the first layer. At this point 20 µl of PBS was dispensed above the NovoGel™ cylinders to keep them wet. Further six NovoGel™ cylinders were deposited on top of layer 1 at positions as shown in FIG. 4 (layer 2). Three HDF cylinders were then deposited at positions 4, 5 and 6 to complete layer 2. After dispensing each HDF cylinder 40 µl of HDF culture medium was dispensed on top of the deposited cylinder to assist the deposition of the subsequent cylinder as well as to prevent dehydration of the cellular cylinders. Next NovoGel™ cylinders for layer 3 were deposited followed by HDF cylinders at positions 3 and 6. Following rewetting of the structure with HDF culture medium, HASMC-HAEC mixed cylinders were laid down in positions 4 and 5. Subsequently, 40 µl of HASMC medium and 40 µl of HDF medium were dispensed on top of the cell cylinders. Layer 4 was completed by depositing NovoGel™ cylinders at positions 1 and 7, HDF cylinders at positions 2 and 6, HASMC-HAEC mixed cylinders at positions 3 and 5, and finally a 4% NovoGel™ cylinder at position 4. Layers 5, 6 and 7 were completed similarly by laying down NovoGel™ cylinders followed by HDF cylinders and finally HASMC-HAEC cylinders at positions shown in FIG. 4. Once the entire construct was completed 0.5 ml of warm NovoGel™ was dispensed over each end of the construct and allowed to gel at room temperature for 5 minutes. Following gelation of that NovoGel™, 30 ml of HASMC medium was added to the Petri dish (to ensure the entire construct was completely submerged). The construct was incubated for 24 hours at 37° C. and 5% $CO_2$ to allow for fusion between the cellular cylinders.

At the end of 24 hours, the surrounding NovoGel™ support structure was removed from the fused multi-layered vascular tube.

Example 3: BioPrinter

A bioprinter was assembled. The bioprinter contained a printer head having a collet chuck grip for holding a cartridge, and a piston for dispensing the contents of the cartridge. The cartridges used were glass microcapillary tubes having a length of 75-85 mm. A new capillary tube was loaded each time bio-ink or support material was required.

In order to print structures, a dispense position repeatability of ±20 µm was required for the duration of the printing process, i.e., when new capillaries were loaded into the printer head. In order to maintain repeatability of all loaded capillary tubes relative to the same point in the x-, y-, and z-directions, the bioprinter contained a laser calibration system for calibrating the position of the microcapillary tube. The laser calibration system calibrated the position of all capillary tips to a common reference location. All printing moves were made relative to this reference position.

All three axes (x-, y-, and z-axes) were calibrated through usage of a single laser distance measurement sensor. The system consisted of a laser sensor and a laser beam. The sensor threshold was the maximum sensing distance of the laser sensor. The sensor was configured to ignore all signals further away than a pre-defined threshold. The sensor used triangulation to determine distance to the object (the capillary tip). The laser sensor was orientated with the beam aimed vertically up (+z-axis).

Vertical Laser Calibration

For Calibration in the X-Axis:

The capillary tip was moved in the range of the laser sensor, with the tip to the left (−x) of the laser beam. The capillary was moved to in the +x direction until the sensor detected the capillary edge, and this position was recorded. The above steps were repeated from the opposite side (i.e., the tip was positioned at the right (+x) of the laser beam and moved in the −x direction until the sensor detected the capillary edge). The positions from both steps were averaged to calculate the mid-point of the capillary. Optionally, the above process was repeated for different y-positions and the calculated mid-points were averaged.

For Calibration in the y-Axis:

The above procedure (for the x-axis) was repeated for the y-axis.

For Calibration in the z-Axis:

The capillary tip was moved to above the sensor beam so that the bean hit the bottom surface of the capillary, and the tip was just outside of the sensor range threshold. The capillary was lowered until the sensor threshold was reached, and that position was recorded as the z-position. Optionally, the above steps were repeated at multiple points on the capillary tip surface and measured heights were averaged.

Horizontal Laser Calibration

For Calibration in the y-Axis:

The capillary was moved so that the tip was just below the laser beam height, and the capillary was off to one side (in the y-direction). The capillary was moved in the y-direction towards the laser. The capillary was stopped when the laser sensor detected the beam reflected off the capillary, and this position was recorded. The above steps were repeated with the capillary off to the other side of the laser, and moved in the −y direction). The mid-point from the above steps was recorded as the y-position.

For Calibration in the x-Axis:

Using the results of the calibration in the y-axis, the y-axis was moved so that the laser was centered on the capillary. The capillary was moved past the sensor threshold and moved towards the sensor. The capillary was stopped as soon as the capillary crossed the sensor threshold and the sensor output changed. This position, plus ½ the capillary width (from the y-calibration) was recorded as the x-position.

For Calibration in the z-Axis:

The capillary was moved up from the x-position until it was clear of the laser beam. The capillary tip was moved down towards the laser beam, and stopped as soon as the laser beam was interrupted (using the same process as for the y-axis). This position was recorded as the z-position.

Capillary Priming

Before printing from a capillary, the bio-ink or support material inside the capillary was primed so that the bio-ink or support material would begin printing at the very tip of the capillary. The calibration laser was used to prime the capillary. The capillary tip was moved just above the laser beam, with the beam centered in the y-axis. The tip was between 20-100 μm above the laser beam. The dispensing piston in the printer head was driven down until the bio-ink or support material started to dispense out of the capillary tip and interrupted the laser beam. The dispensed bio-ink or support material was aspirated back into the capillary tube by driving the piston in the reverse direction (20-100 μm). The capillary was then primed and ready to dispense.

NovoGel™ Capillary Cleaning

NovoGel™ was used as a support material. In order to remove excess NovoGel™ sticking to the outside surface of the capillary tube and to avoid the excess NovoGel™ from affecting print quality, the excess NovoGel™ was removed. A wiping feature was integrated into a bulk NovoGel™ vessel. A bulk NovoGel™ vessel was fitted with a standard medical vial with an open cap for a septum to be attached. A septum was configured with a cross cut in the center of 1-2 mm thick silicone. By dipping the capillary into the bulk NovoGel™ vessel through the septum and aspirating NovoGel™, excess NovoGel™ was wiped from the capillary as it exited the vessel, and remained in the bulk vessel.

Printing of a Vascular Structure

The bioprinter and cartridge was assembled as above. The bioprinter had a stage having a Petri dish for receiving structures generated by the bioprinter. The Petri dish was coated with NovoGel™.

A two dimensional representation (see e.g., FIG. 4) of a vascular structure was inputted by a user into a software program into a computer which was connected to the bioprinter. The two dimensional representation of the vascular structure consisted of rods of HASMC-HAEC mixed cellular cylinders, HDF cylinders, and NovoGel™ rods defining the voids of the vascular structure and surrounding the vascular structure. HASMC-HAEC mixed cellular cylinders and HDF cellular cylinders were prepared as in Example 1, and aspirated into capillary tubes for insertion into the collet chuck of the printer head. Alternatively, capillary tubes were loaded into the printer head and dipped into the bulk NovoGel™ vessel and NovoGel™ was aspirated into the capillary tube. The capillary tubes were calibrated using the vertical laser calibration system.

When the commands from the software program were provided to the bioprinter, the bioprinter would print the three-dimensional structure, alternating between HASMC-HAEC rods, HDF rods and NovoGel™ rods, onto the Petri dish, in predetermined locations. See Example 2. After each rod was laid down on the Petri dish, the rod was wetted with a small amount of culture medium. Once the entire construct was completed warm NovoGel™ was dispensed over each end of the construct and allowed to gel at room temperature, and cell culture medium was added to the Petri dish to submerge the entire construct. The construct was then incubated at 37° C. and 5% $CO_2$ to allow for fusion between the cellular cylinders. At the end of the incubation time, the surrounding NovoGel™ support structure was removed from the fused multi-layered vascular tube.

While the invention has been described in connection with specific embodiments thereof, it will be understood that the inventive methodology is capable of further modifications. This patent application is intended to cover any variations, uses, or adaptations of the invention following, in general, the principles of the invention and including such departures from the present disclosure as come within known or customary practice within the art to which the invention pertains and as may be applied to the essential features herein before set forth and as follows in scope of the appended claims.

What is claimed is:

1. A bio-ink cartridge for use with an automated bio-printer, the bio-ink cartridge comprising:
   a bio-ink comprising a plurality of human cells and a cell culture media, the plurality of human cells comprise multicellular aggregates, at least a first multicellular aggregate is cohered to at least a second multicellular aggregate, the bio-ink is a cell suspension;
   a deposition orifice, wherein the bio-ink is primed with respect to the deposition orifice; and
   wherein the bio-ink cartridge is attachable to an automated bio-printer and the bio-ink cartridge is controllable by the automated bio-printer, wherein the bio-ink is primed with respect to the deposition orifice using a laser beam.

2. The bio-ink cartridge of claim 1, wherein the bio-ink is a homologous ink.

3. The bio-ink cartridge of claim 1, wherein the bio-ink is a heterologous ink.

4. The bio-ink cartridge of claim 1, wherein the plurality of human cells further comprise differentiated cells.

5. The bio-ink cartridge of claim 1, wherein the plurality of human cells further comprise non-differentiated cells.

6. The bio-ink cartridge of claim 1, wherein the plurality of human cells further comprise a mixture of differentiated cells and non-differentiated cells.

7. The bio-ink cartridge of claim 5, wherein the non-differentiated cells comprise stem cells.

8. The bio-ink cartridge of claim 7, wherein the stem cells comprise progenitor cells.

9. The bio-ink cartridge of claim 7, wherein the stem cells comprise pluripotent cells.

10. The bio-ink cartridge of claim 1, wherein the cell culture media comprises lipids.

11. The bio-ink cartridge of claim 1, wherein the cell culture media comprises cytokines.

12. The bio-ink cartridge of claim 1, wherein the cell culture media comprises sugars.

13. The bio-ink cartridge of claim 1, wherein the cell culture media comprises vitamins.

14. The bio-ink cartridge of claim 1, wherein the cell culture media comprises amino acids.

15. The bio-ink cartridge of claim 1, wherein the bio-ink further comprises an extrusion compound, the extrusion compound is a hydrogel, the bio-ink is extrudable, and the bio-ink is shaped by the deposition orifice when the bio-ink is extruded through the deposition orifice.

16. The bio-ink cartridge of claim 1, wherein the plurality of human cells comprise liver cells.

17. The bio-ink cartridge of claim 1, wherein the plurality of human cells comprise kidney cells.

18. The bio-ink cartridge of claim 1, wherein the bio-ink is a semi-solid composition.

19. The bio-ink cartridge of claim 1, wherein the bio-ink has a viscosity of about 1,000 centipoise to about 400,000 centipoise.

20. The bio-ink cartridge of claim 1, wherein the deposition orifice further comprises an inner diameter of about 1 μm to about 1000 μm.

21. The bio-ink cartridge of claim 1, wherein the bio-ink is primed by compacting and advancing the bio-ink until it is located in a position in contact with the dispensing orifice.

\* \* \* \* \*